(12) United States Patent
Tada et al.

(10) Patent No.: US 9,865,829 B2
(45) Date of Patent: Jan. 9, 2018

(54) ORGANIC ELECTROLUMINESCENT ELEMENT MATERIAL AND ORGANIC ELECTROLUMINESCENT ELEMENT USING SAME

(71) Applicant: NIPPON STEEL & SUMIKIN CHEMICAL CO., LTD., Tokyo (JP)

(72) Inventors: Masashi Tada, Kitakyushu (JP); Takahiro Kai, Kitakyushu (JP); Tohru Asari, Kitakyushu (JP); Junya Ogawa, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 831 days.

(21) Appl. No.: 14/362,402

(22) PCT Filed: Nov. 22, 2012

(86) PCT No.: PCT/JP2012/080303
§ 371 (c)(1),
(2) Date: Jun. 2, 2014

(87) PCT Pub. No.: WO2013/088934
PCT Pub. Date: Jun. 20, 2013

(65) Prior Publication Data
US 2014/0332792 A1 Nov. 13, 2014

(30) Foreign Application Priority Data
Dec. 12, 2011 (JP) ................. 2011-271173

(51) Int. Cl.
| | |
|---|---|
| C07F 5/02 | (2006.01) |
| C07F 7/08 | (2006.01) |
| C07F 19/00 | (2006.01) |
| C09K 11/06 | (2006.01) |
| H01L 51/50 | (2006.01) |
| H05B 33/14 | (2006.01) |
| H01L 51/00 | (2006.01) |
| H05B 33/20 | (2006.01) |

(52) U.S. Cl.
CPC ............ *H01L 51/0094* (2013.01); *C07F 5/02* (2013.01); *C09K 11/06* (2013.01); *H01L 51/008* (2013.01); *H01L 51/0067* (2013.01); *H01L 51/0074* (2013.01); *H01L 51/5012* (2013.01); *H05B 33/14* (2013.01); *H05B 33/20* (2013.01); *H01L 51/0085* (2013.01); *H01L 51/5016* (2013.01); *H01L 51/5056* (2013.01); *H01L 51/5072* (2013.01); *H01L 51/5096* (2013.01)

(58) Field of Classification Search
CPC .......... C07F 5/02; C09K 11/06; H05B 33/14; H01L 51/5032
USPC .............................................. 568/4
See application file for complete search history.

(56) References Cited

U.S. PATENT DOCUMENTS

| | | | | |
|---|---|---|---|---|
| 3,254,096 | A * | 5/1966 | Dupont ................... | C07F 5/027 149/19.2 |
| 6,838,574 | B1 * | 1/2005 | Endo ....................... | C07F 5/027 560/102 |
| 7,067,653 | B2 * | 6/2006 | Vicente .............. | A61K 41/0095 540/145 |
| 9,164,382 | B2 * | 10/2015 | Hwang ................... | G03F 7/028 |
| 2011/0147722 | A1 | 6/2011 | Hawker et al. | |

FOREIGN PATENT DOCUMENTS

JP 2005-166574 A 6/2005

OTHER PUBLICATIONS

International Search Report for the Application No. PCT/JP2012/080303 dated Feb. 19, 2013.
International Preliminary Report on Patentability (PCT/IPEA/409) for Application No. PCT/JP2012/080303.
Dash, Barada P. et al., "Synthesis and Properties of Carborane-Appended $C_3$-Symmetrical Extended $\pi$ Systems", Journal of American Chemical Society, 2010, vol. 132, No. 18, pp. 6578-6587.
Peterson, Joseph J. et al., "Investigating Carboranes in Conjugated Polymers", Polymer Preprints, 2010, vol. 51, No. 2, pp. 545-546.
Wang, Yu-Man et al., "Synthesis, characterization, and reactions of 6,13-disubstituted 2,3,9,10-tetrakis(trimethylsilyl)pentacene derivatives", Tetrahedron, 2007, vol. 63, pp. 8586-8597.

* cited by examiner

*Primary Examiner* — Venkataraman Balasubramanian
(74) *Attorney, Agent, or Firm* — Cheng Law Group, PLLC

(57) ABSTRACT

Provided is an organic electroluminescent device (organic EL device) with improved luminous efficiency, sufficiently ensured driving stability, and a simple construction. The organic electroluminescent device includes an anode, an organic layer, and a cathode laminated on a substrate, in which at least one organic layer selected from the group consisting of a light-emitting layer, a hole-transporting layer, an electron-transporting layer, an electron-blocking layer, and a hole-blocking layer contains a carborane compound that has at least one carborane ring with a silyl group on the carbon thereof.

9 Claims, 2 Drawing Sheets

ORGANIC ELECTROLUMINESCENT ELEMENT MATERIAL AND ORGANIC ELECTROLUMINESCENT ELEMENT USING SAME

TECHNICAL FIELD

The present invention relates to a novel organic electroluminescent device material and an organic electroluminescent device using the material, and specifically, to a thin-film-type device that emits light when an electric field is applied to a light-emitting layer formed of an organic compound.

BACKGROUND ART

In general, an organic electroluminescent device (hereinafter referred to as "organic EL device") is constructed of a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, optimization of kinds of electrodes has been attempted for the purpose of improving efficiency of injection of carriers from the electrodes. As a result, there has been developed a device in which a hole-transporting layer formed of an aromatic diamine and a light-emitting layer formed of an 8-hydroxyquinoline aluminum complex (hereinafter referred to as "Alq3") are formed between electrodes as thin films, resulting in a significant improvement in luminous efficiency, as compared to conventional devices in which a single crystal of anthracene or the like is used. Thus, development of the above-mentioned organic EL device has been promoted in order to accomplish its practical application to a high-performance flat panel having features such as self-luminescence and rapid response.

Further, studies have been made on using phosphorescent light rather than fluorescent light as an attempt to raise luminous efficiency of a device. Many kinds of devices including the above-mentioned device in which a hole-transporting layer formed of an aromatic diamine and a light-emitting layer formed of Alq3 are formed emit light by using fluorescent light emission. However, by using phosphorescent light emission, that is, by using light emission from a triplet excited state, luminous efficiency is expected to be improved by about three times to four times, as compared to the case of using conventional devices in which fluorescent light (singlet) is used. In order to accomplish this purpose, studies have been made on adopting a coumarin derivative or a benzophenone derivative as a light-emitting layer, but extremely low luminance has only been provided. Further, studies have been made on using a europium complex as an attempt to use a triplet state, but highly efficient light emission has not been accomplished. In recent years, many studies centered on an organic metal complex such as an iridium complex have been made, as disclosed in Patent Literature 1, for the purpose of attaining high luminous efficiency and a long lifetime.

CITATION LIST

Patent Literature

[PTL 1] JP 2003-515897 A
[PTL 2] WO 01/041512 A
[PTL 3] JP 2005-166574 A

Not only the dopant material but also a host material to be used is important for obtaining high luminous efficiency. A typical material that has been proposed as the host material is, for example, 4,4'-bis(9-carbazolyl)biphenyl (hereinafter referred to as "CBP") as a carbazole compound introduced in Patent Literature 2. When CBP is used as a host material for a green phosphorescent light-emitting material typified by a tris(2-phenylpyridine) iridium complex (hereinafter referred to as "Ir(ppy) 3"), owing to the characteristic of CBP by which the flow of a hole is facilitated and the flow of an electron is made difficult, a charge injection balance is broken and excessive holes flow out to an electron-transporting layer side. As a result, the efficiency of light emission from Ir(ppy) 3 reduces.

As described in the foregoing, a host material having a high triplet excitation energy and balanced injecting/transporting characteristics for both charges (a hole and an electron) is needed for obtaining high luminous efficiency in an organic EL device. Further, a compound that is electrochemically stable, and has high heat resistance and excellent amorphous stability has been desired, and hence an additional improvement has been required.

Patent Literature 3 discloses such a carborane compound as shown below as an electron-transporting material for an organic EL device.

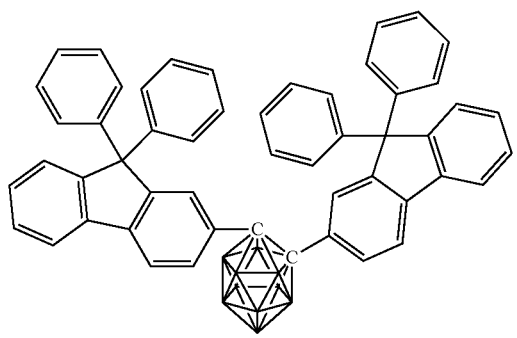

However, the disclosed carborane compound is merely a compound having an aromatic hydrocarbon group on the carbon of a carborane, and the usefulness of a compound having a silyl group on one carbon of a carborane as an organic EL device material is not disclosed.

Patent Literature 3 discloses such a carborane compound as shown below as an electron-transporting material for an organic EL device.

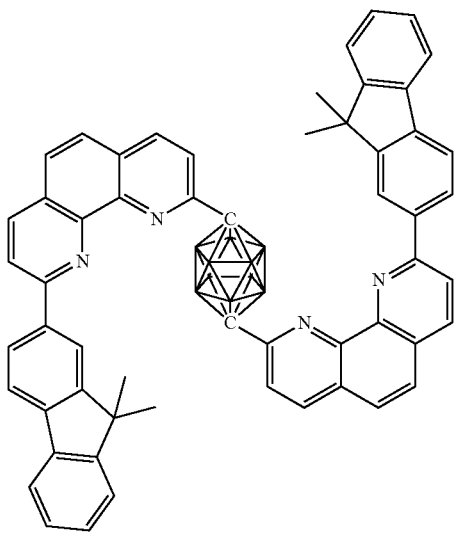

However, the disclosed carborane compound is merely a compound having an aromatic heterocyclic group on the carbon of a carborane, and the usefulness of a compound having a silyl group on one carbon of a carborane as an organic EL device material is not disclosed.

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device, which has high efficiency, has high driving stability, and is practically useful and an organic EL device material suitable for the organic EL device.

As a result of their extensive studies, the inventors of the present invention have found that the use of a compound having a silyl group on one carbon of a carborane as an organic EL device material allows a device to show excellent characteristics, and have completed the present invention.

The present invention relates to an organic electroluminescent device material, including a carborane compound represented by the general formula (1).

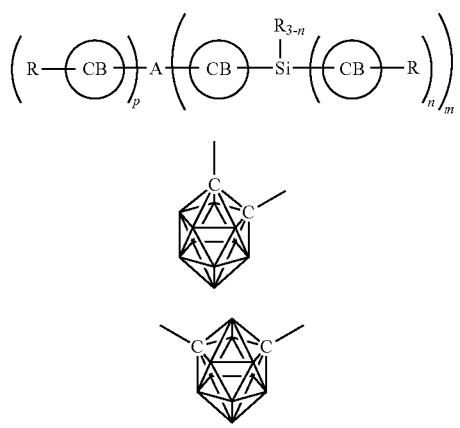

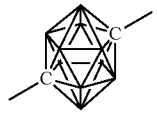

In the general formula (1): a ring CB represents a divalent carborane group —$C_2B_{10}H_{10}$— represented by any one of the formula (a), the formula (b), and the formula (c), and when a plurality of rings CB are present in a molecule, the rings may be identical to or different from each other; R represents hydrogen, a substituted or unsubstituted aliphatic hydrocarbon group having 1 to 12 carbon atoms, a substituted or unsubstituted aromatic hydrocarbon group having 6 to 50 carbon atoms, or a substituted or unsubstituted aromatic heterocyclic group having 3 to 50 carbon atoms, and a plurality of R's may be identical to or different from each other; A represents a direct bond, hydrogen, a substituted or unsubstituted aliphatic hydrocarbon group having 1 to 12 carbon atoms, a substituted or unsubstituted $Si(R)_d$ group, a substituted or unsubstituted aromatic hydrocarbon group having 6 to 50 carbon atoms, or a substituted or unsubstituted aromatic heterocyclic group having 3 to 50 carbon atoms, provided that A does not represent hydrogen except when p+m represents 1, A does not represent a direct bond except when p+m represents 2, and A represents a p+m-valent group when A represents a group except hydrogen and a direct bond, R of the $Si(R)_d$ group has the same meaning as that of the R, and d represents an integer represented by 4−(p+m); and p represents an integer of from 0 to 3, m represents an integer of from 1 to 4, n represents an integer of from 0 to 3, and p+m represents an integer of from 1 to 4.

An example of the carborane compound represented by the general formula (1) is a carborane compound represented by the general formula (2).

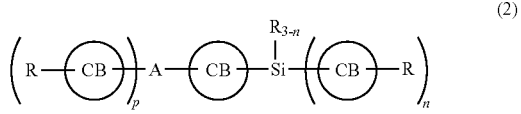

In the general formula (2), a ring CB, R, and A have the same meanings as those of the ring CB, R, and A of the general formula (1), p represents an integer of from 0 to 3, and n represents an integer of from 0 to 3.

In the general formula (1), it is preferred that the ring CB represent a divalent carborane group represented by the formula (b). It is also preferred that m represent 1 or p represent 0.

The present invention also relates to an organic electroluminescent device, including: a substrate; an anode; an organic layer; and a cathode, the anode, the organic layer, and the cathode being laminated on the substrate, in which the organic layer includes at least one layer selected from the group consisting of a light-emitting layer, a hole-transporting layer, an electron-transporting layer, an electron-blocking layer, and a hole-blocking layer, the at least one layer containing the organic electroluminescent device material according to any one of claims 1 to 4. Here, it is preferred that the organic electroluminescent device material be present in a light-emitting layer containing a phosphorescent light-emitting dopant.

DESCRIPTION OF EMBODIMENTS

Figure 1:
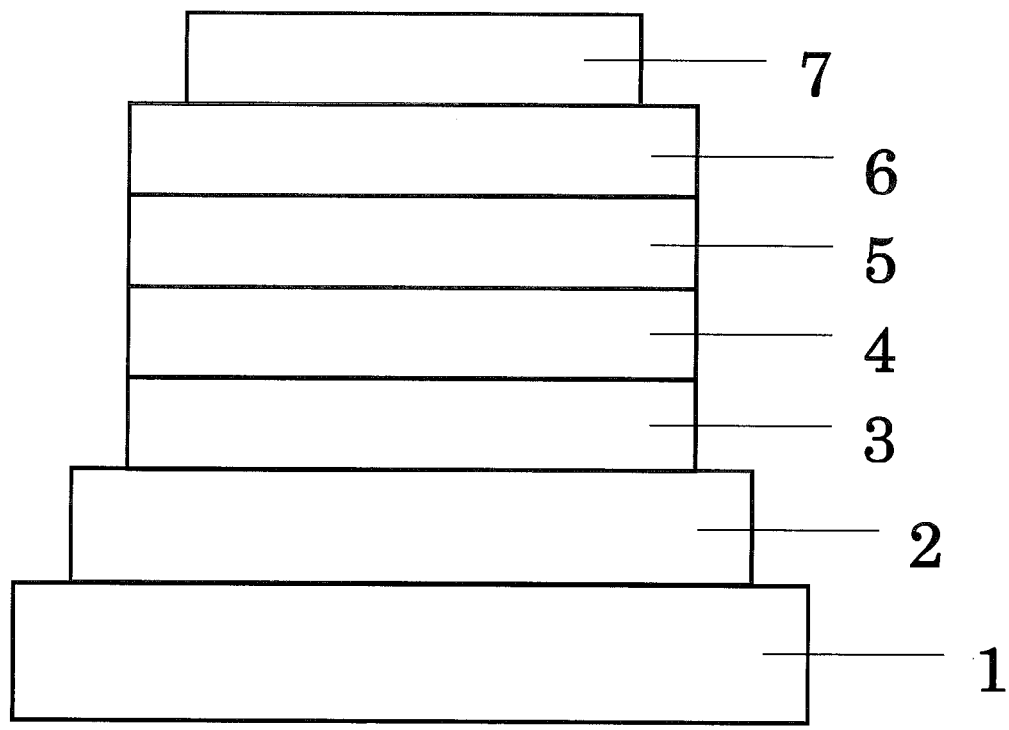
FIG. 1 is a sectional view illustrating a structural example of an organic EL device.

An organic EL device material of the present invention is a carborane compound represented by the general formula (1). The carborane compound has, as its basic skeleton, a spherical structure (ring CB) formed of 2 carbon atoms and 10 boron atoms, the structure being represented by any one of the formulae (a), (b), and (c). For example, when the relationships of p=0, m=1, and n=0 are satisfied in the carborane compound represented by the general formula (1), the compound is A-(ring CB)—SiR$_3$, i.e., can be represented by a molecular formula "A-C$_2$H$_{10}$B$_{10}$—SiR$_3$." A divalent carborane group is represented by any one of the formulae (a), (b), and (c), and has a chemical formula "—C$_2$H$_{10}$B$_{10}$—." Hereinafter, the divalent carborane group represented by the formula (a), (b), or (c) is also referred to as "carborane group (a), (b), or (c)."

In the general formula (1), p represents an integer of 0 to 3, m represents an integer of 1 to 4, n represents an integer of 0 to 3, and p+m represents an integer of 1 to 4. It is preferred that p represent 1 or 2 and m represent 1, p represent 0 and m represent 1 or 2, or p+m represent 2 or 3, and that n represent 0 to 2.

In addition, a preferred example of the general formula (1) is the general formula (2). Another preferred example of the general formula (1) is the case where the ring CB is the carborane group (b).

Symbols common to the general formulae (1) and (2) have the same meaning. R represents hydrogen, a substituted or unsubstituted aliphatic hydrocarbon group having 1 to 12 carbon atoms, a substituted or unsubstituted aromatic hydrocarbon group having 6 to 50 carbon atoms, or a substituted or unsubstituted aromatic heterocyclic group having 3 to 50 carbon atoms, and when a plurality of R's exist, the R's may be identical to or different from each other.

When R represents an aliphatic hydrocarbon group, specific examples thereof include a methyl group, an ethyl group, a propyl group, a butyl group, a hexyl group, a heptyl group, an octyl group, a nonyl group, and a decyl group, and the group may be linear, branched, or alicyclic. An aliphatic hydrocarbon group having 1 to 8 carbon atoms is preferred. Specific examples thereof include a methyl group, an ethyl group, a propyl group, a butyl group, a pentyl group, a hexyl group, a cyclohexyl group, and a methylcyclohexyl group.

When the aliphatic hydrocarbon group has a substituent, the total number of its substituents is 1 to 6, preferably 1 to 4, more preferably 1 to 2. In addition, when the substituent has 2 or more substituents, the substituents may be identical to or different from each other. In addition, when the aliphatic hydrocarbon group has a substituent, the number of carbon atoms of the substituent is included in the calculation of the number of carbon atoms of the group.

Preferred examples of the substituent include an alkoxy group having 1 to 6 carbon atoms, an acyl group having 2 to 7 carbon atoms, an aryl group having 6 to 18 carbon atoms, and a heteroaryl group having 3 to 18 carbon atoms. More preferred examples of the substituent include an alkoxy group having 1 to 4 carbon atoms, an acyl group having 2 to 5 carbon atoms, an aryl group having 6 to 12 carbon atoms, or a heteroaryl group having 3 to 12 carbon atoms. Specific examples thereof may include a methoxy group, an ethoxy group, a propoxy group, a butoxy group, a hexyloxy group, an acetyl group, a propionyl group, a phenyl group, a naphthyl group, a pyridyl group, a piperidyl group, a triazyl group, an indolyl group, a carbazolyl group, a benzofuranyl group, a dibenzofuranyl group, a benzothiophenyl group, and a dibenzothiophenyl group.

Next, the case where R represents an aromatic hydrocarbon group or an aromatic heterocyclic group is described.

The aromatic hydrocarbon group or the aromatic heterocyclic group is an aromatic hydrocarbon group having 6 to 50 carbon atoms or an aromatic heterocyclic group having 3 to 50 carbon atoms. Specific example thereof include monovalent groups produced by removing one hydrogen atom from benzene, naphthalene, fluorene, pyridine, pyrimidine, triazine, indole, quinoline, isoquinoline, quinoxaline, naphthyridine, carbazole, indolocarbazole, acridine, phenanthroline, phenazine, benzofuran, dibenzofuran, xanthene, oxanthrene, phenoxazine, benzothiophene, dibenzothiophene, thioxanthene, thianthrene, phenoxathiin, phenothiazine, or an aromatic compound in which a plurality of these compounds are linked. Of those, monovalent groups produced by removing one hydrogen atom from an aromatic compound selected from the following compounds are preferred: benzene, pyridine, triazine, carbazole, dibenzofuran, and dibenzothiophene. Monovalent groups produced by removing one hydrogen atom from an aromatic compound selected from benzene and carbazole, or from an aromatic compound in which a plurality of these compounds are linked are more preferred. When the plurality of aromatic compounds are linked, the compounds may be identical to or different from each other. In the case of a group produced from an aromatic compound in which a plurality of aromatic rings are linked, the number of the rings to be linked is preferably 2 to 5, more preferably 2 or 3. Specific examples of the group produced by removing hydrogen from the aromatic compound in which the plurality of aromatic rings are linked include biphenyl, terphenyl, phenylpyridine, diphenylpyridine, bipyridine, diphenylpyrimidine, diphenyltriazine, phenylnaphthalene, diphenylnaphthalene, and diphenylfluorene.

When the aromatic hydrocarbon group or the aromatic heterocyclic group has a substituent, the total number of its substituents is 1 to 10, preferably 1 to 6, more preferably 1 to 4. In addition, when the substituent has 2 or more substituents, the substituents may be identical to or different from each other. In addition, in the calculation of the number of carbon atoms of the aromatic hydrocarbon group or the aromatic heterocyclic group, when any such group has a substituent, the number of carbon atoms of the substituent is included.

Preferred examples of the substituent include an alkyl group having 1 to 10 carbon atoms, a cycloalkyl group having 3 to 10 carbon atoms, an alkoxy group having 1 to 6 carbon atoms, an acyl group having 2 to 7 carbon atoms, and a diarylamino group having 12 to 24 carbon atoms. More preferred examples thereof include an alkyl group having 1 to 4 carbon atoms, a cycloalkyl group having 3 to 8 carbon atoms, an alkoxy group having 1 to 4 carbon atoms, an acyl group having 2 to 5 carbon atoms, and a diarylamino group having 12 to 20 carbon atoms, and specific examples thereof can include a methyl group, an ethyl group, a propyl group, a butyl group, a cyclopentyl group, a cyclohexyl group, a methylcyclohexyl group, a methoxy group, an ethoxy group, a propoxy group, a butoxy group, a hexyloxy group, an acetyl group, a propionyl group, and a diphenylamino group.

In the general formulae (1) to (3), A represents a direct bond, hydrogen, a p+m-valent, substituted or unsubstituted aliphatic hydrocarbon group having 1 to 12 carbon atoms, a p+m-valent Si(R) group, a p+m-valent, substituted or unsubstituted aromatic hydrocarbon group having 6 to 50 carbon atoms, or a p+m-valent, substituted or unsubstituted aromatic heterocyclic group having 3 to 50 carbon atoms, provided that when p+m represents an integer of 2 or more, A does not represent hydrogen, and when p+m represents an integer except 2, A does not represent a direct bond. In addition, even when p+m represents 1 or 2, A may represent a p+m-valent group except hydrogen and a direct bond. R of the Si(R)$_d$ group has the same meaning as that described above and d represents an integer calculated from 4−(p+m).

When A represents a p+m-valent, substituted or unsubstituted aliphatic hydrocarbon group, a specific example thereof is interpreted as a group obtained by removing p+m−1 hydrogen atoms from an aliphatic hydrocarbon group in the description for R, and when the group has a substituent, the substituent is the same as that described above.

When A represents an Si(R)$_d$ group, the total number d of R's on its Si is represented by 4−(p+m), and when the number of R's is 2 or more, the R's may be identical to or different from each other. Specific examples of the R are the same as those in the description for R in the general formula (1), and when the R has a substituent, the substituent is the same as that described above.

Preferred examples of R in the Si(R) a group include an alkyl group having 1 to 10 carbon atoms, a cycloalkyl group having 3 to 10 carbon atoms, an alkoxy group having 1 to 6 carbon atoms, an aryl group having 6 to 18 carbon atoms, and a heteroaryl group having 3 to 18 carbon atoms. More preferred examples thereof include an alkyl group having 1 to 8 carbon atoms, a cycloalkyl group having 3 to 8 carbon atoms, an alkoxy group having 1 to 4 carbon atoms, an aromatic hydrocarbon group having 6 to 12 carbon atoms, and an aromatic heterocyclic group having 3 to 14 carbon atoms. Specific examples thereof may include a methyl group, an ethyl group, a propyl group, a butyl group, a cyclopentyl group, a cyclohexyl group, a methylcyclohexyl group, a methoxy group, an ethoxy group, a propoxy group, a butoxy group, a hexyloxy group, a phenyl group, a naphthyl group, a pyridyl group, a piperidyl group, a triazyl group, an indolyl group, a carbazolyl group, a benzofuranyl group, a dibenzofuranyl group, a benzothiophenyl group, and a dibenzothiophenyl group.

Next, when A represents a p+m-valent, substituted or unsubstituted aromatic hydrocarbon group or aromatic heterocyclic group, the group is interpreted as a group obtained by removing p+m−1 hydrogen atoms from the aromatic hydrocarbon group or aromatic heterocyclic group in the description for R, and when the group has a substituent, the substituent is the same as that described above.

Of the skeletons represented by the general formulae (1) and (2), a skeleton in which a substituent on a carborane is represented by an alkyl group can be synthesized by the following reaction formula with reference to a synthesis example described in J. Org. Chem. 1999, 64, 1045.

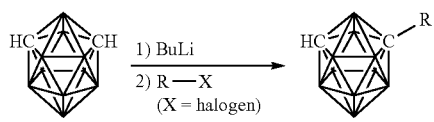

Of the skeletons represented by the general formulae (1) and (2), a skeleton in which a substituent on a carborane is represented by an aromatic hydrocarbon group or an aromatic heterocyclic group can be synthesized by the following reaction formula with reference to a synthesis example described in Inorg. Chem. 2011, 50, 5485.

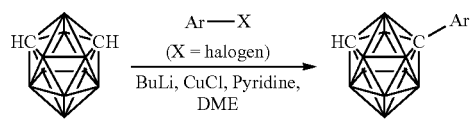

Specific examples of the compounds represented by the general formulae (1) and (2) are shown below, but the compounds are not limited to these examples.

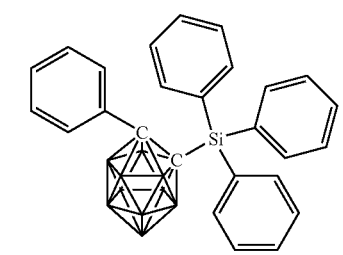

1

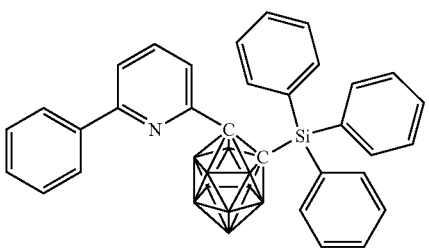

2

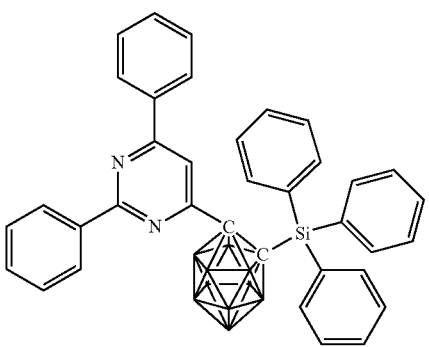

3

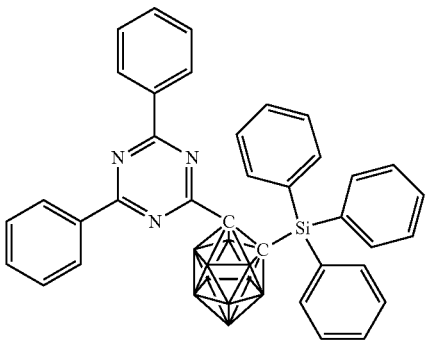

4

5
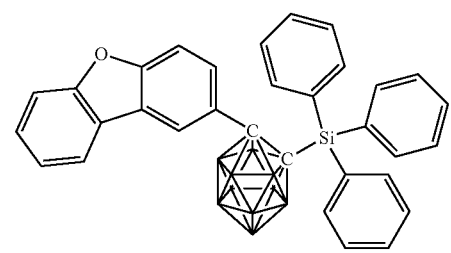
6
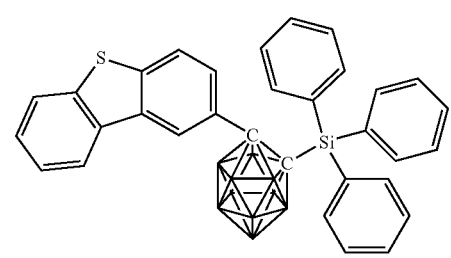
7
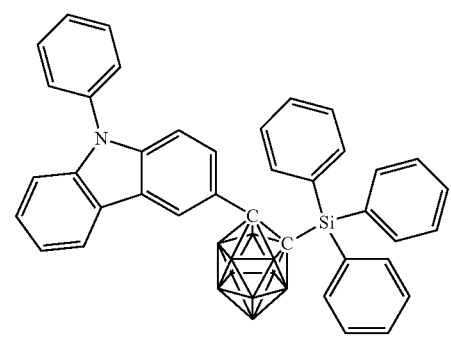
8
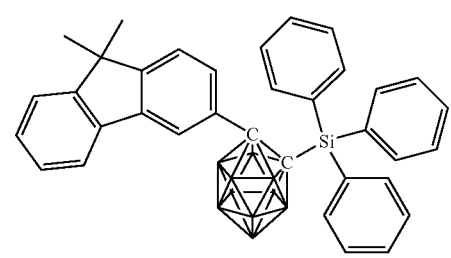
9
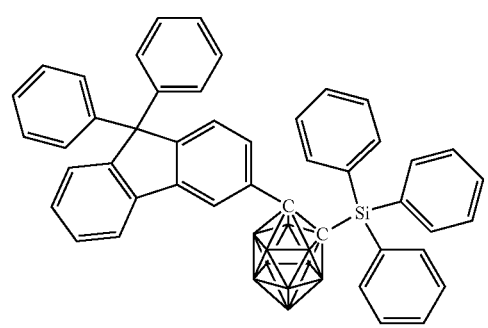
10
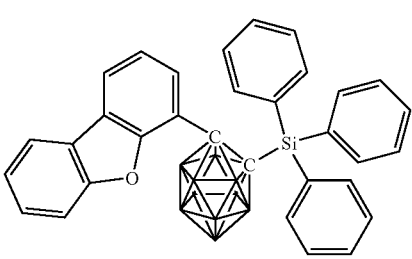
11
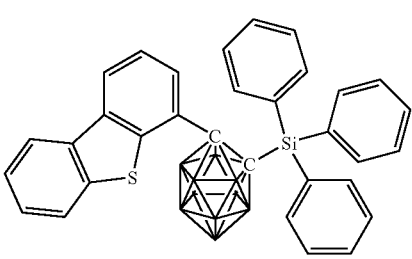
12
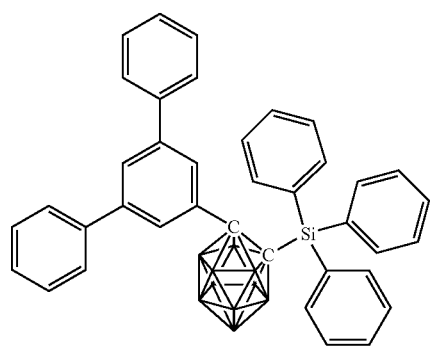
13
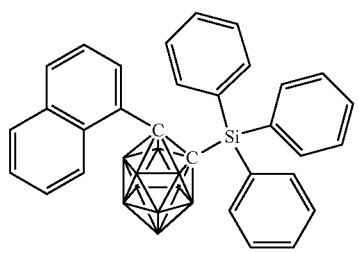
14
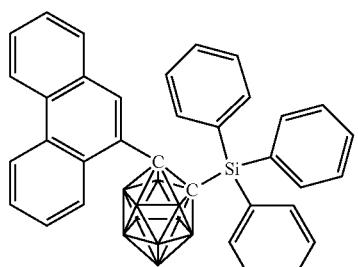
15
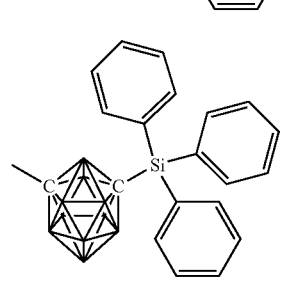

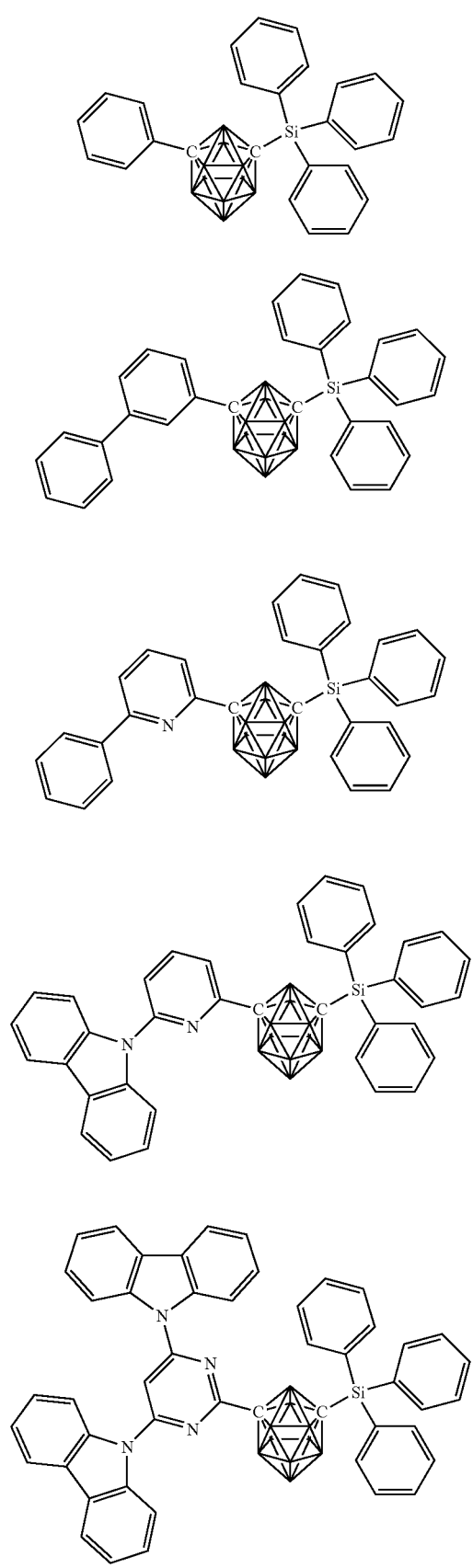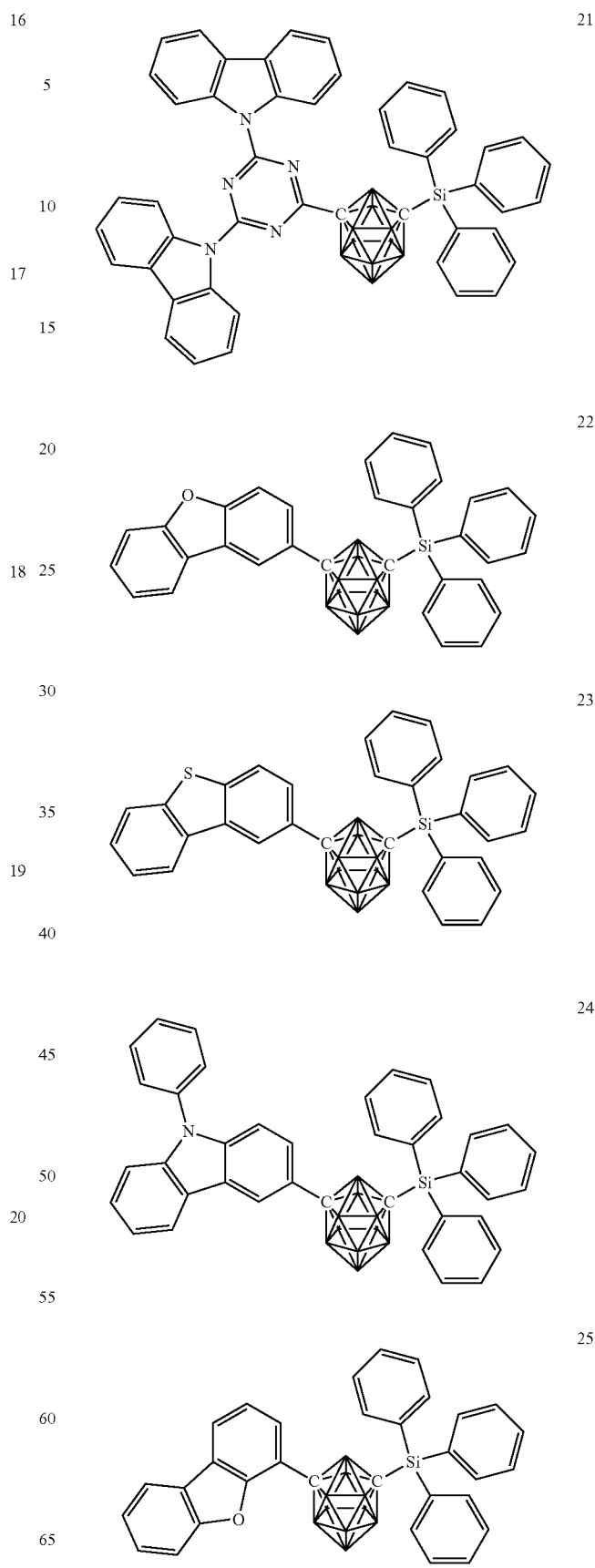

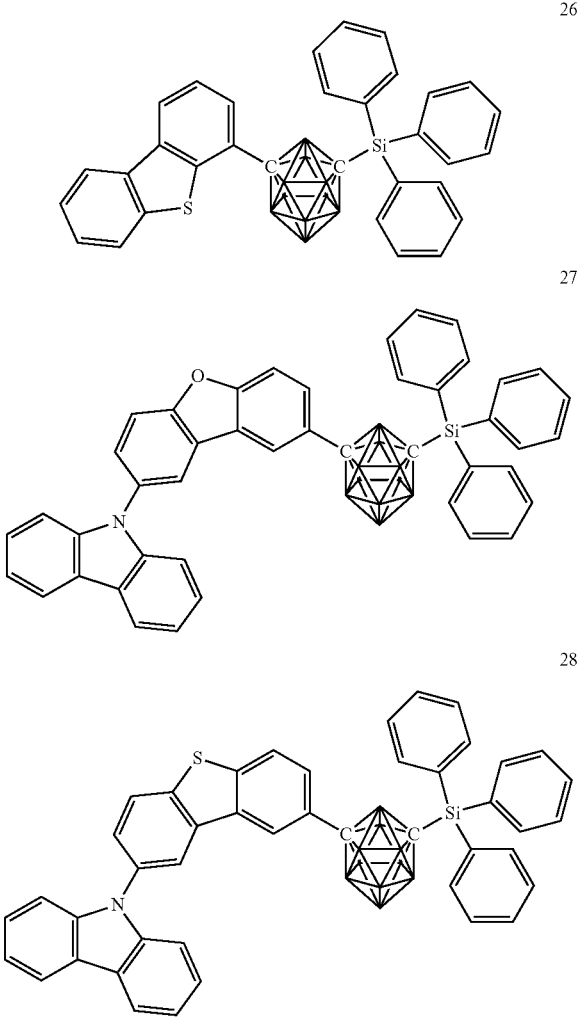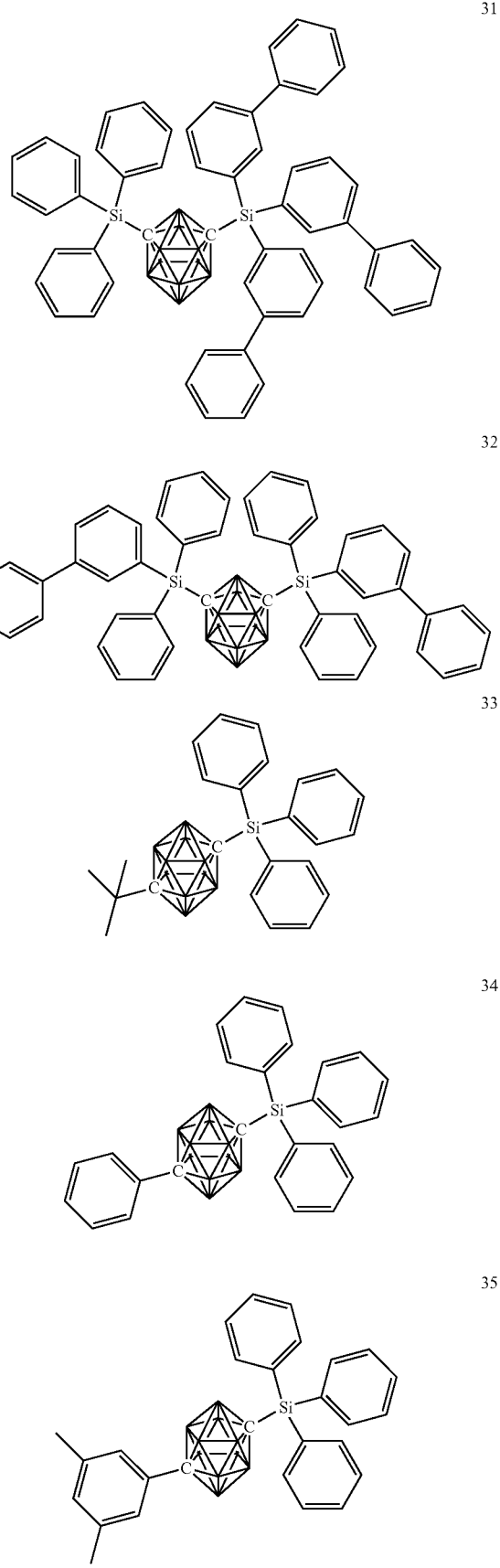

36
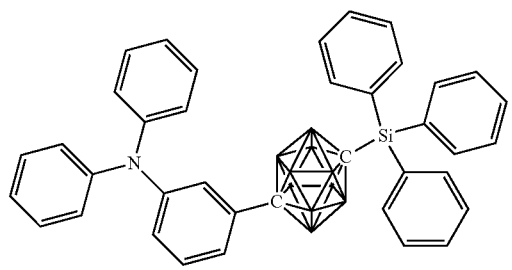
37
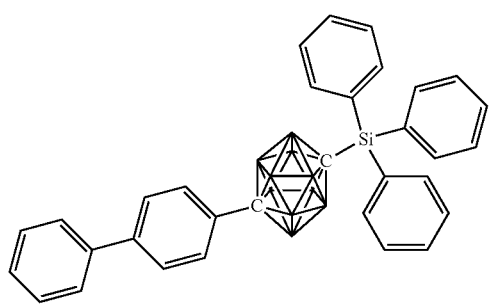
38
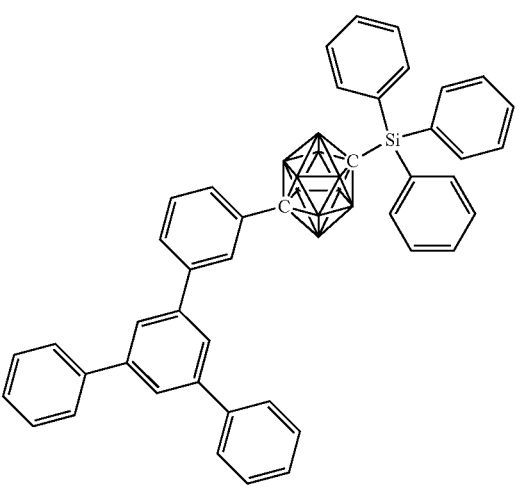
39
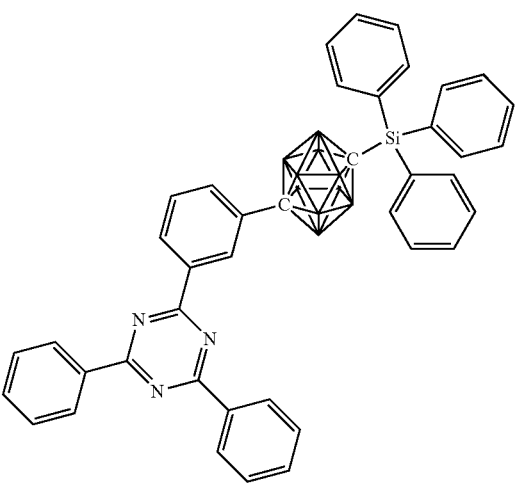
40
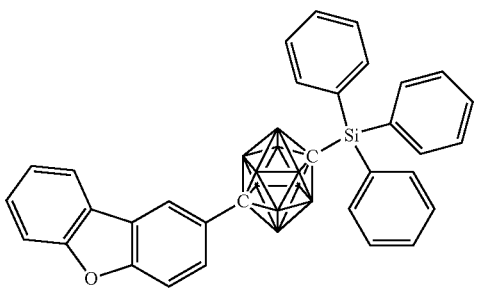
41
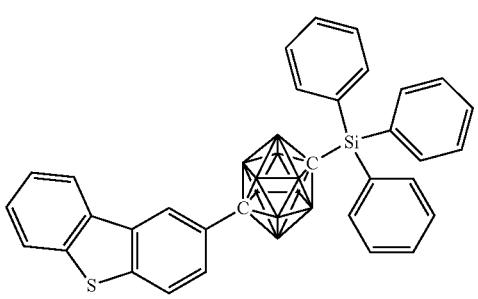
42
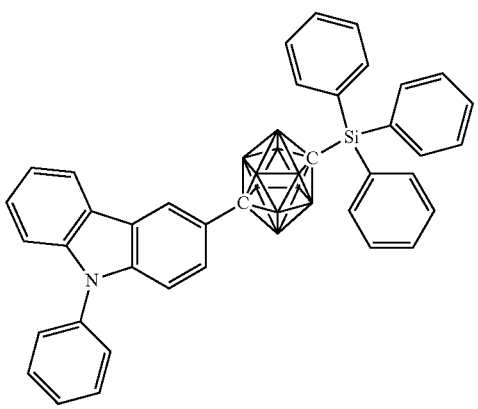
43
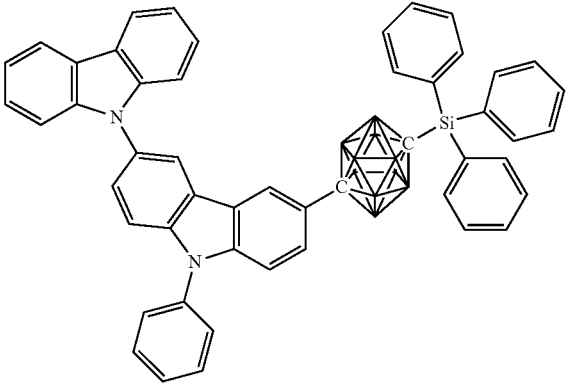

44
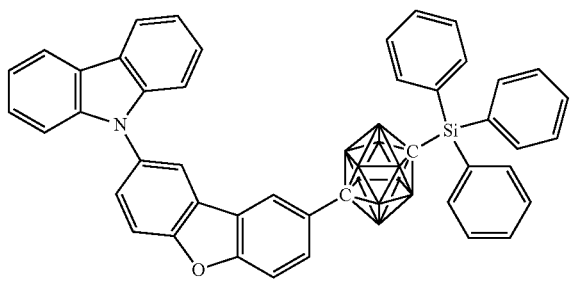
45
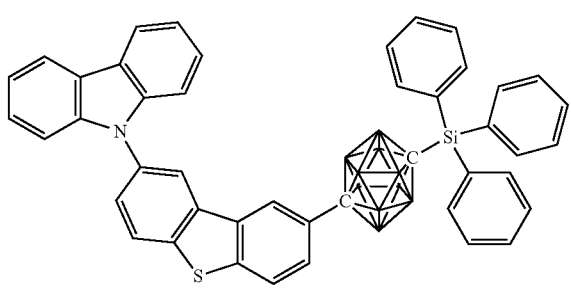
46
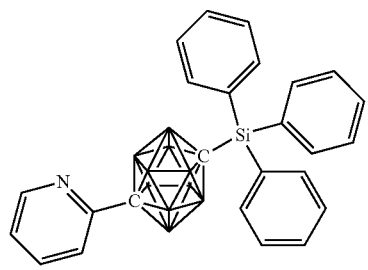
47
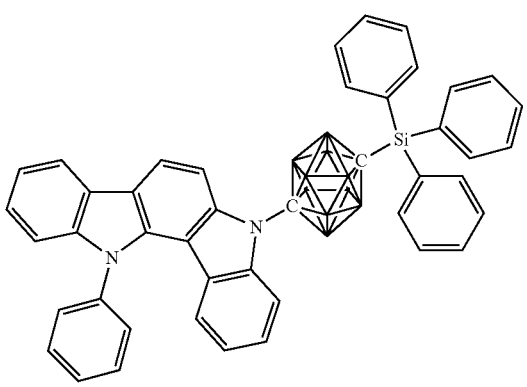
48
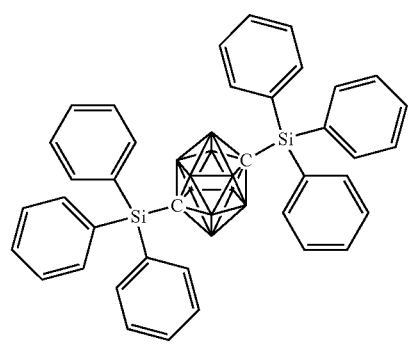
49
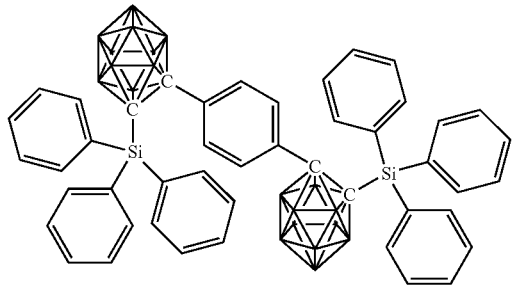
50
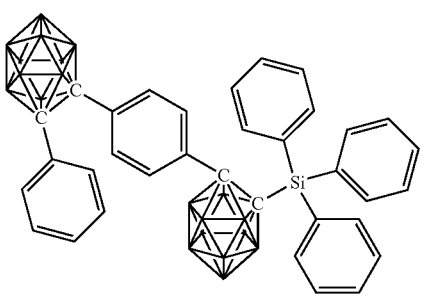
51
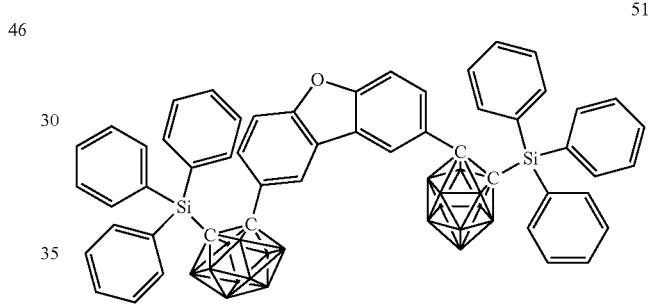
52
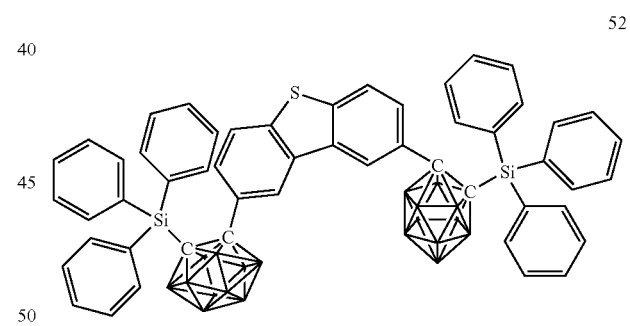
53
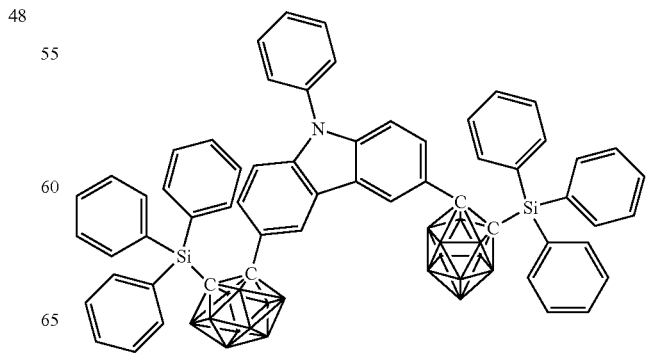

54
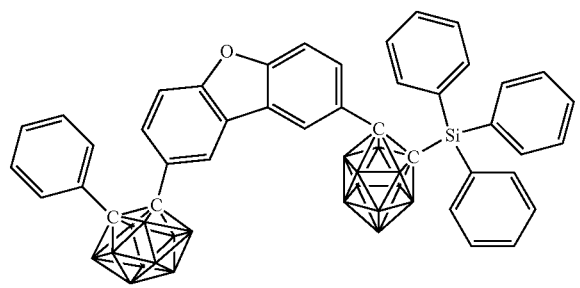
55
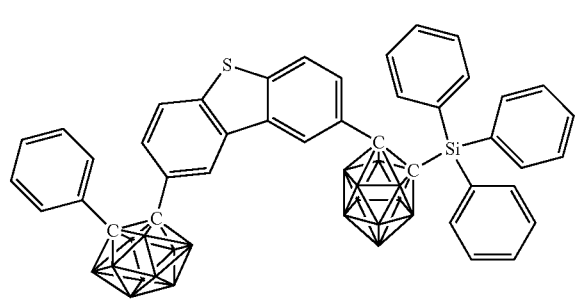
56
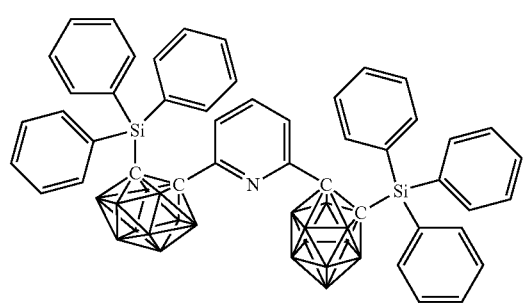
57
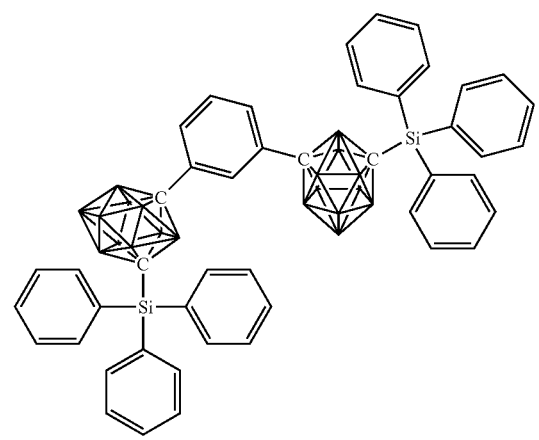
58
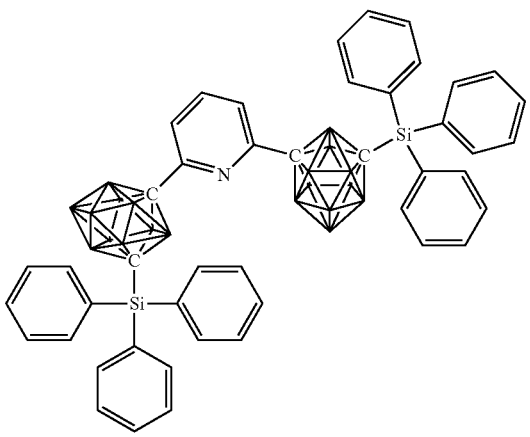
59
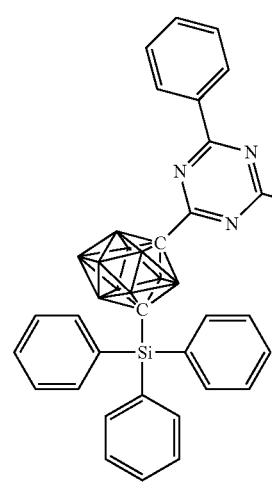
60
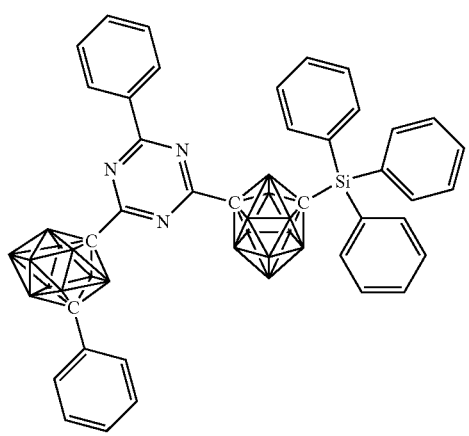

61
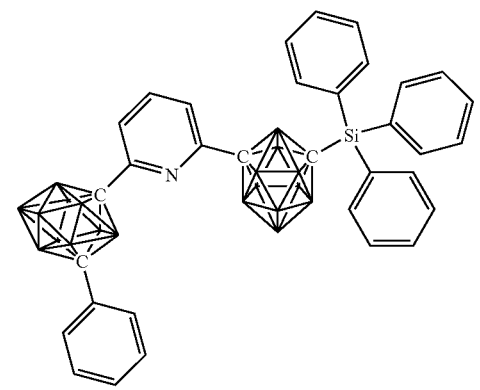
62
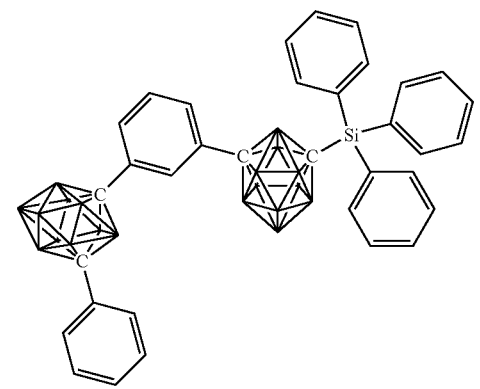
63
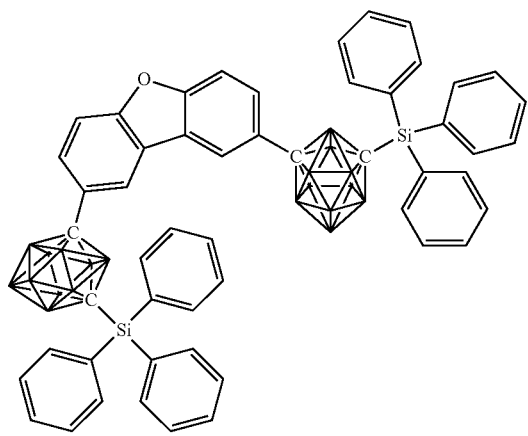
64
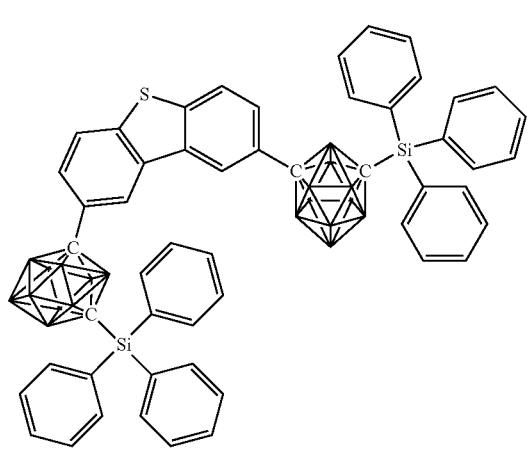
65
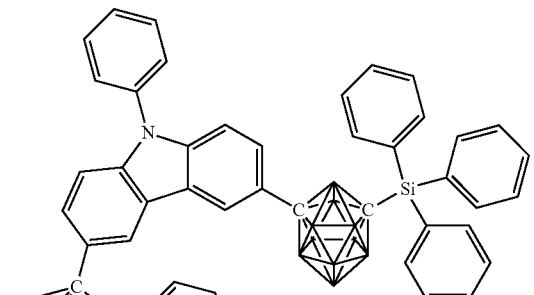
66
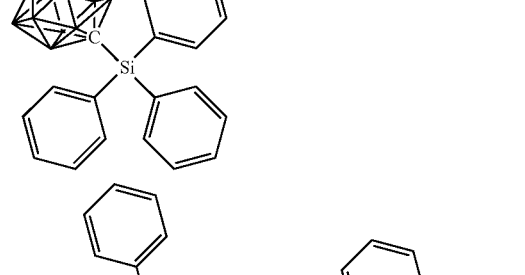
67
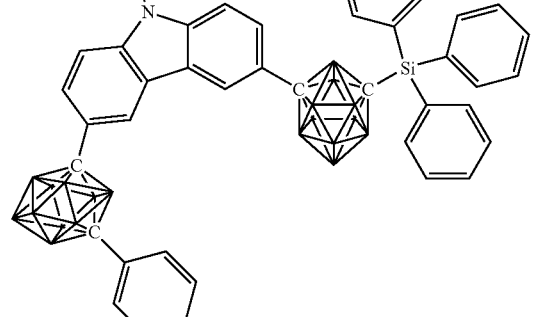
68
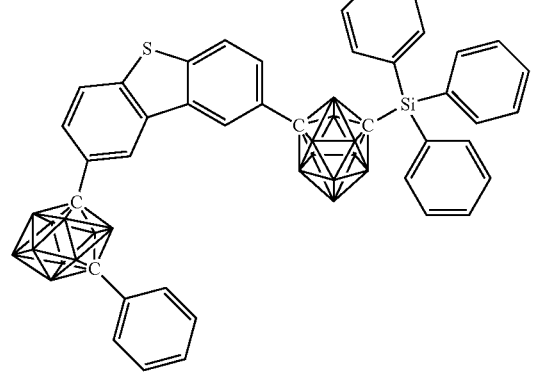

-continued
69
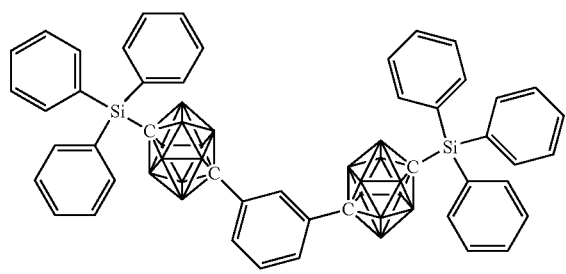
70
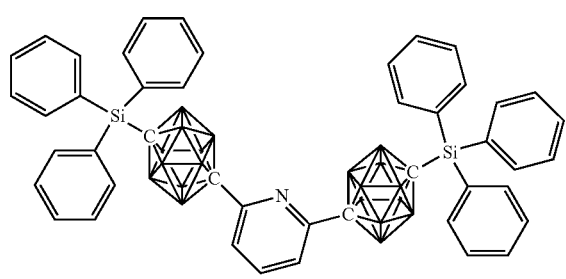
71
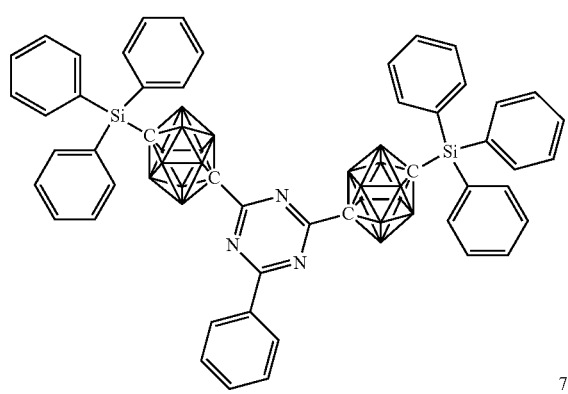
72
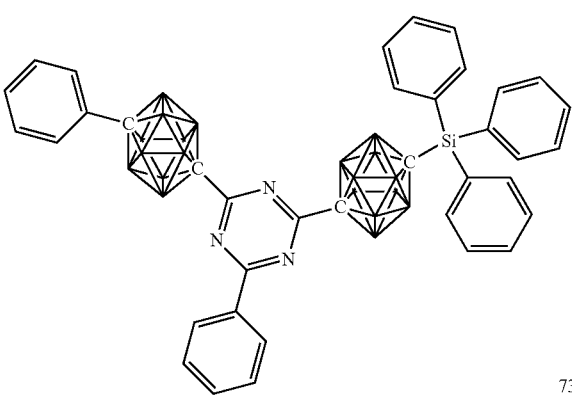
73
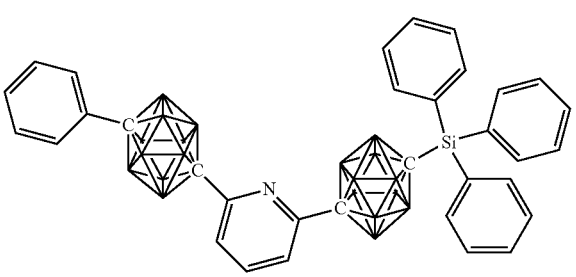
-continued
74
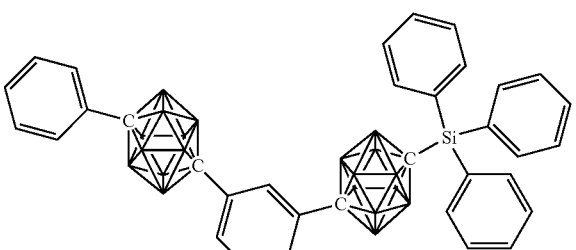
75
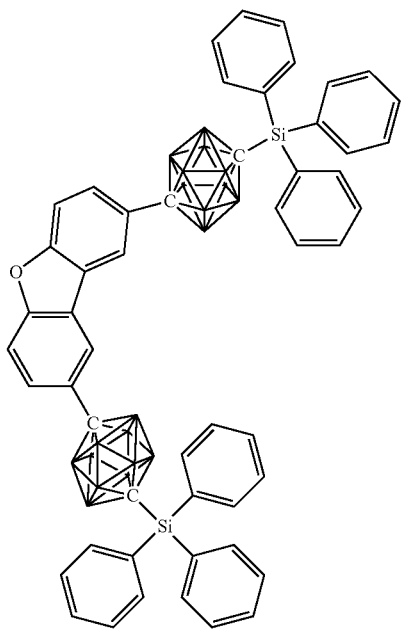
76
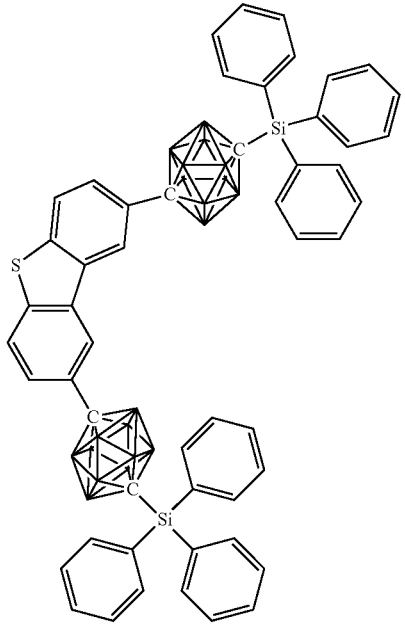

77
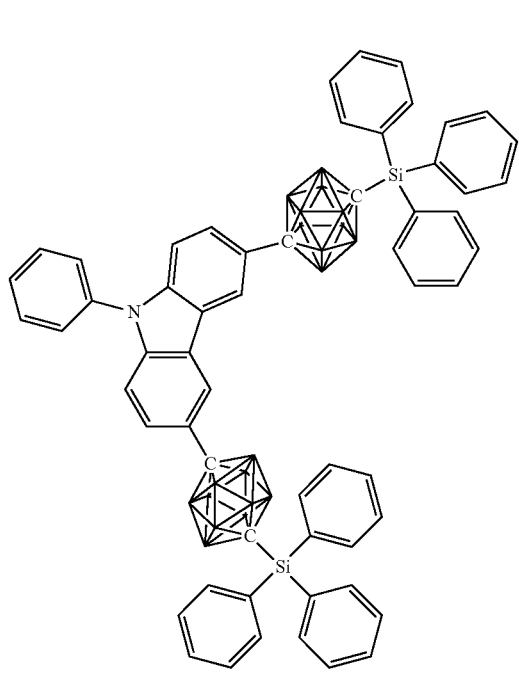
78
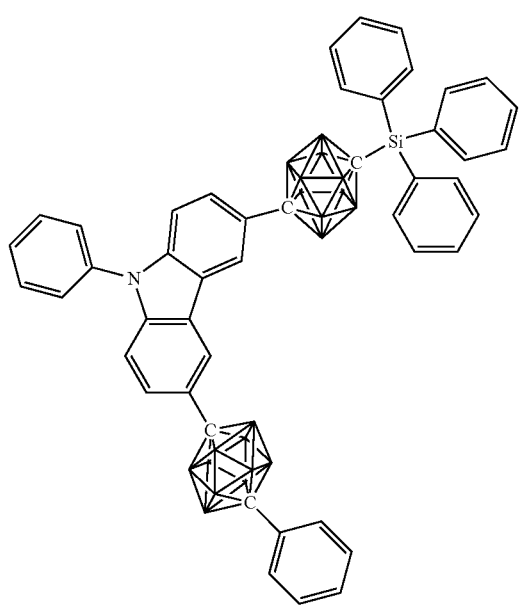
79
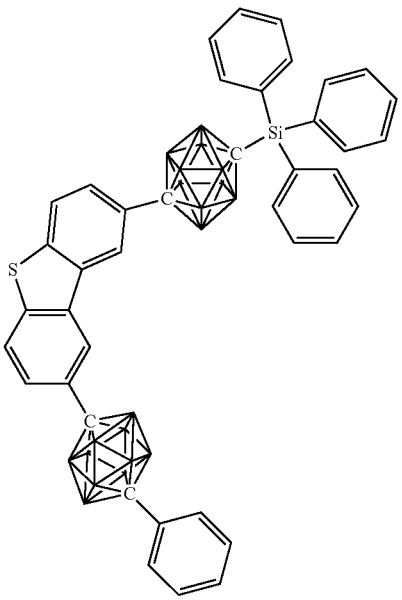
80
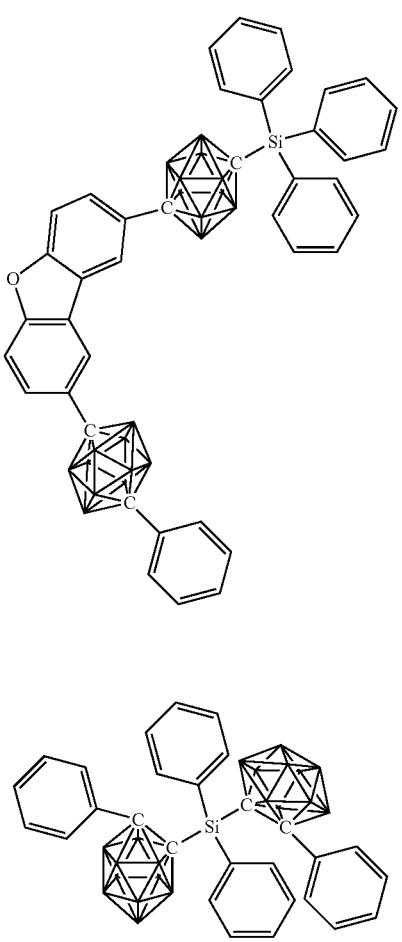
81

82
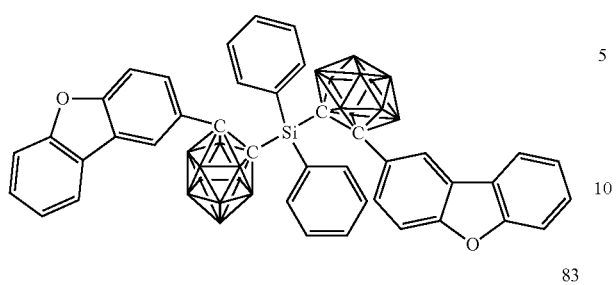
83
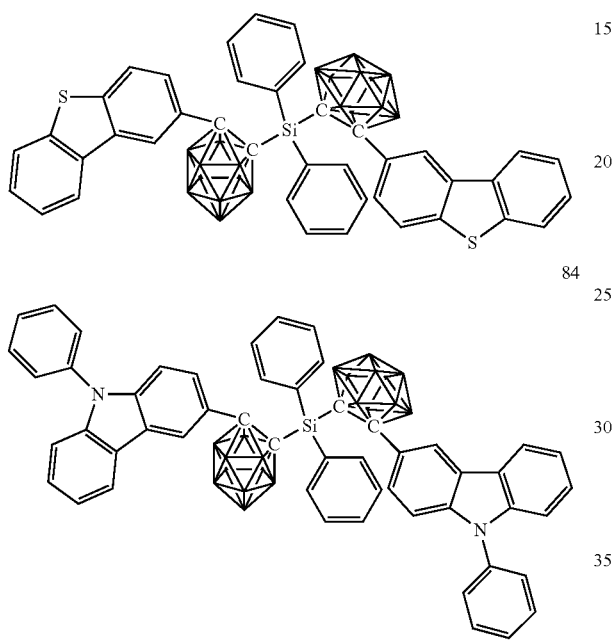
84
85
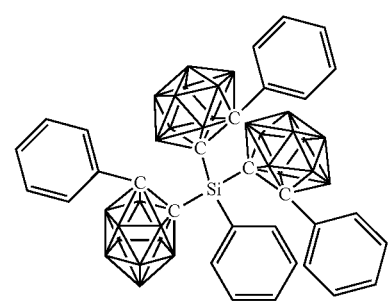
86
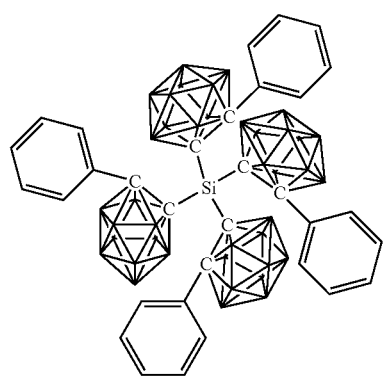
87
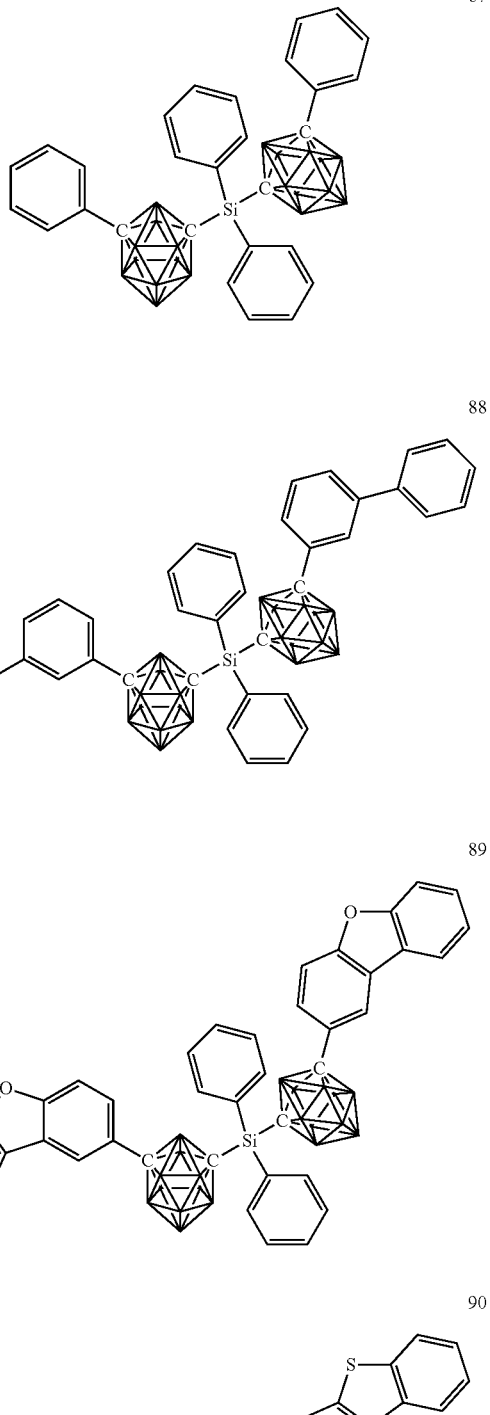
88
89
90
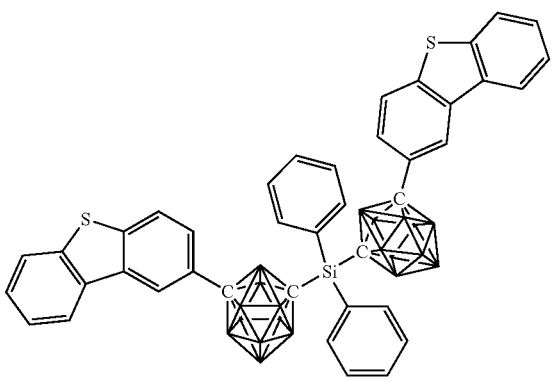

91
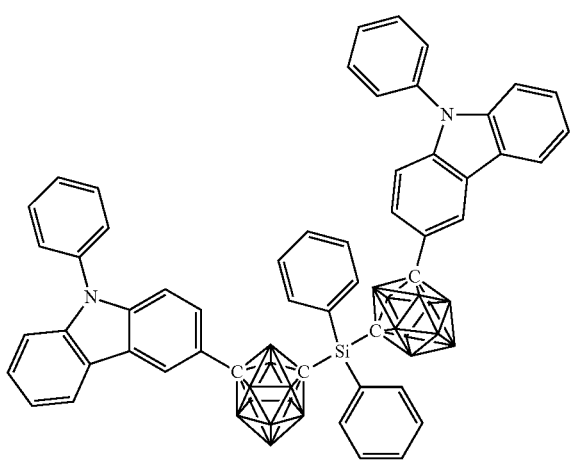
92
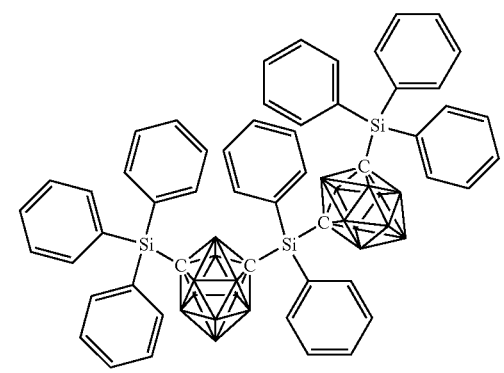
93
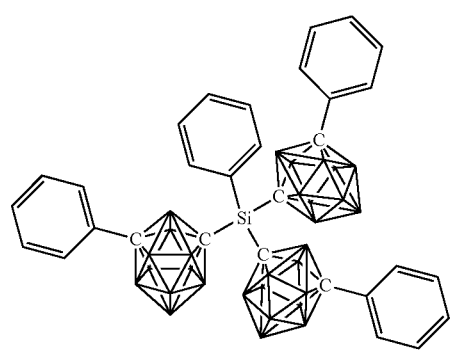
94
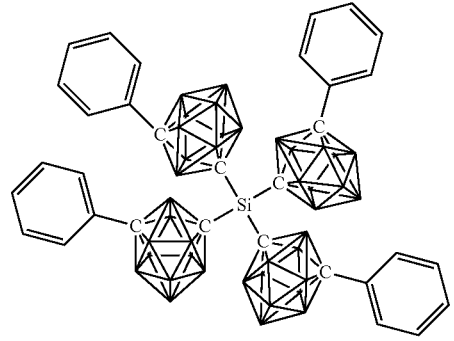
95
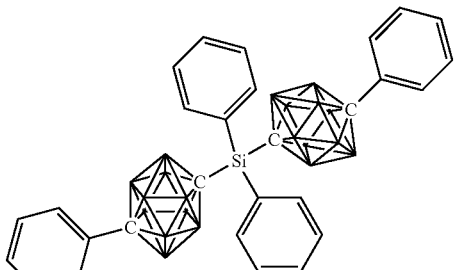
96
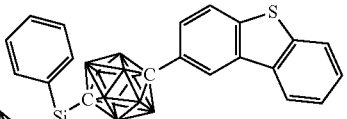
97
98
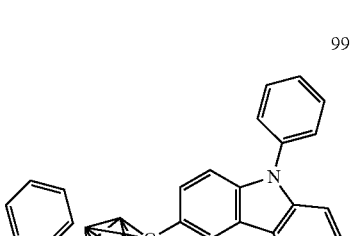
99

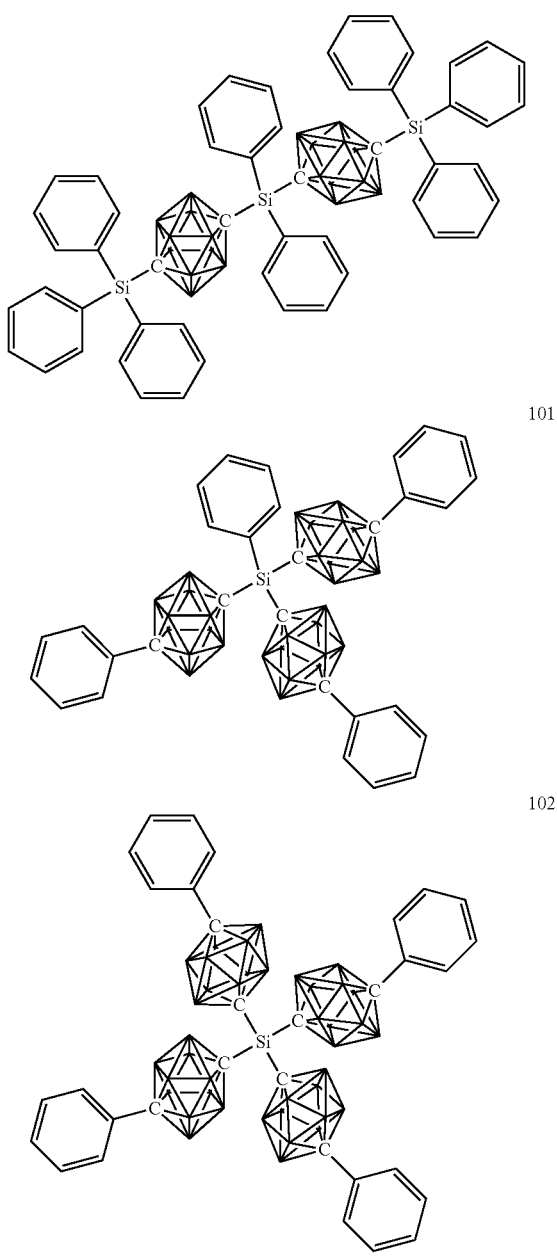

When the carborane compound represented by the general formula (1) is incorporated into at least one organic layer in an organic EL device formed by laminating an anode, a plurality of organic layers, and a cathode on a substrate, an excellent organic EL device is provided. The organic layers preferably include at least a light-emitting layer, and preferably further include a hole-transporting layer, an electron-transporting layer, a hole-blocking layer, or an electron-blocking layer. A light-emitting layer, a hole-transporting layer, an electron-transporting layer, a hole-blocking layer, or an electron-blocking layer is suitable as the organic layer into which the carborane compound is incorporated. Here, when the carborane compound is used in the light-emitting layer, the compound can be used as a host material for a light-emitting layer containing a fluorescent light-emitting, delayed fluorescent light-emitting, or phosphorescent light-emitting dopant. In addition, the carborane compound can be used as an organic light-emitting material that radiates fluorescence and delayed fluorescence. The carborane compound is more preferably incorporated as a host material for a light-emitting layer containing a phosphorescent light-emitting dopant.

The organic EL device of the present invention includes organic layers including at least one light-emitting layer between an anode and a cathode laminated on a substrate. In addition, at least one of the organic layers contains the carborane compound. The carborane compound represented by the general formula (1) is advantageously contained in the light-emitting layer together with a phosphorescent light-emitting dopant.

Next, the structure of the organic EL device of the present invention is described with reference to the drawings. However, the structure of the organic EL device of the present invention is by no means limited to one illustrated in the drawings.

FIG. 1 is a sectional view illustrating a structural example of a general organic EL device. Reference numerals 1, 2, 3, 4, 5, 6, and 7 represent a substrate, an anode, a hole-injecting layer, a hole-injecting layer, a light-emitting layer, an electron-transporting layer, and a cathode, respectively. The organic EL device of the present invention may include an exciton-blocking layer adjacent to the light-emitting layer, or may include an electron-blocking layer between the light-emitting layer and a hole-transporting layer. The exciton-blocking layer may be inserted on any of the anode side and the cathode side of the light-emitting layer, and may also be inserted simultaneously on both sides. The organic EL device of the present invention includes the substrate, the anode, the light-emitting layer, and the cathode as its essential layers. The organic EL device of the present invention preferably includes a hole-injecting/transporting layer and an electron-injecting/transporting layer in addition to the essential layers, and more preferably includes a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure as compared to FIG. 1, that is, a structure formed by laminating the layers on the substrate 1 in the order of the cathode 7, the electron-transporting layer 6, the light-emitting layer 5, the hole-transporting layer 4, and the cathode. In this case as well, a layer may be added or eliminated as required.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which may be used for manufacturing an amorphous, transparent conductive film. In order to produce the anode, it may be possible to form any of those electrode substances into a thin film by using a method such as vapor deposition or sputtering and form a pattern having a desired shape thereon by photolithography. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred $\Omega/\square$ or less. Further, the thickness of the resultant film is, depending on the material used, selected from usually the range of from 10 to 1,000 nm, preferably the range of from 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Suitable specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, a lithium/aluminum mixture, and aluminum. The cathode may be produced by forming any of those electrode substances into a thin film by using a method such as vapor deposition or sputtering. Further, the sheet resistance as the cathode is preferably several hundred $\Omega/\square$ or less, and the thickness of the resultant film is selected from usually the range of from 10 nm to 5 µm, preferably the range of from 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer is a layer that emits light after the production of an exciton by the recombination of a hole injected from the anode and an electron injected from the cathode, and the light-emitting layer desirably contains an organic light-emitting material and a host material.

When the light-emitting layer is a fluorescent light-emitting layer, a fluorescent light-emitting material can be used alone in the light-emitting layer. However, it is preferred that the fluorescent light-emitting material be used as a fluorescent light-emitting dopant and the host material be mixed.

The carborane compound represented by the general formula (1) can be used as the fluorescent light-emitting material in the light-emitting layer. However, the fluorescent light-emitting material is known through, for example, many patent literatures, and hence can be selected therefrom. Examples thereof include a benzoxazole derivative, a benzothiazole derivative, a benzimidazole derivative, a styrylbenzene derivative, a polyphenyl derivative, a diphenylbutadiene derivative, a tetraphenylbutadiene derivative, a naphthalimide derivative, a coumarine derivative, a condensed aromatic compound, a perinone derivative, an oxadiazole derivative, an oxazine derivative, an aldazine derivative, a pyrrolidine derivative, a cyclopentadiene derivative, a bisstyrylanthracene derivative, a quinacridone derivative, a pyrrolopyridine derivative, a thiadiazolopyridine derivative, a styrylamine derivative, a diketopyrrolopyrrole derivative, an aromatic dimethylidene compound, various metal complexes typified by a metal complex of a 8-quinolinol derivative, and a metal complex, rare earth complex, or transition metal complex of a pyrromethene derivative, polymer compounds such as polythiophene, polyphenylene, and polyphenylene vinylene, and an organic silane derivative. Of those, for example, the following compound is preferred: a condensed aromatic compound, a styryl compound, a diketopyrrolopyrrole compound, an oxazine compound, or a pyrromethene metal complex, transition metal complex, or lanthanoid complex. For example, the following compound is more preferred: naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, anthanthrene, naphtho[2,1-f]isoquinoline, α-naphthaphenanthridine, phenanthroxazole, quinolino[6,5-f]quinoline, or benzothiophanthrene. Those compounds may each have an alkyl group, aryl group, aromatic heterocyclic group, or diarylamino group as a substituent.

The carborane compound represented by the general formula (1) can be used as a fluorescent host material in the light-emitting layer. However, the fluorescent host material is known through, for example, many patent literatures, and hence can be selected therefrom. For example, the following material can be used: a compound having a condensed aryl ring such as naphthalene, anthracene, phenanthrene, pyrene, chrysene, naphthacene, triphenylene, perylene, fluoranthene, fluorene, or indene, or a derivative thereof; an aromatic amine derivative such as N,N'-dinaphthyl-N,N'-diphenyl-4,4'-diphenyl-1,1'-diamine; a metal chelated oxinoid compound typified by tris(8-quinolinato)aluminum (III); a bisstyryl derivative such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; thiadiazolopyridine derivative; a dibenzofuran derivative; a carbazole derivative; an indolocarbazole derivative; a triazine derivative; or a polymer-based derivative such as a polyphenylene vinylene derivative, a poly-p-phenylene derivative, a polyfluorene derivative, a polyvinyl carbazole derivative, or a polythiophene derivative. However, the fluorescent host material is not particularly limited thereto. Further, a plurality of kinds of host materials may be used in combination.

When the fluorescent light-emitting material is used as a fluorescent light-emitting dopant and the host material is contained, the content of the fluorescent light-emitting dopant in the light-emitting layer desirably falls within the range of from 0.01 to 20 wt %, preferably from 0.1 to 10 wt %.

An organic EL device typically injects charges from both of its electrodes, i.e., its anode and cathode into a light-emitting substance to produce a light-emitting substance in an excited state, and causes the substance to emit light. In the case of a charge injection-type organic EL device, 25% of the produced excitons are said to be excited to a singlet excited state and the remaining 75% are said to be excited to a triplet excited state. As described in Advanced Materials 2009, 21, 4802-4806, it has been known that after a specific fluorescent light-emitting substance has undergone an energy transition to a triplet excited state as a result of intersystem crossing or the like, the substance is subjected to inverse intersystem crossing to a singlet excited state by triplet-triplet annihilation or the absorption of a thermal energy to radiate fluorescence, thereby expressing thermally activated delayed fluorescence. The organic EL device of the present invention can also express delayed fluorescence. In this case, the light emission can include both fluorescent light emission and delayed fluorescent light emission, provided that light emission from the host material may be present in part of the light emission.

When the light-emitting layer is a delayed fluorescent light-emitting layer, a delayed fluorescent light-emitting material can be used alone in the light-emitting layer. However, it is preferred that the delayed fluorescent light-emitting material be used as a delayed fluorescent light-emitting dopant and the host material be mixed.

Although the carborane compound represented by the general formula (1) can be used as the delayed fluorescent light-emitting material in the light-emitting layer, a material selected from known delayed fluorescent light-emitting materials can also be used. Examples thereof include a tin complex, an indolocarbazole derivative, a copper complex, and a carbazole derivative. Specific examples thereof include, but not limited to, compounds described in the following non patent literatures and patent literature.

Adv. Mater. 2009, 21, 4802-4806, Appl. Phys. Lett. 98, 083302 (2011), JP 2011-213643 A, and J. Am. Chem. Soc. 2012, 134, 14706-14709.

Specific examples of the delayed fluorescent light-emitting material are shown below, but the delayed fluorescent light-emitting material is not limited to the following compounds.

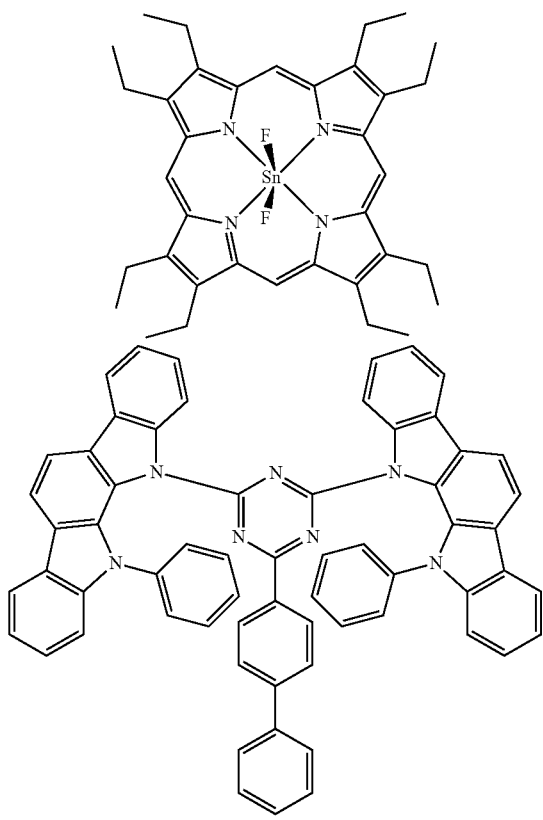

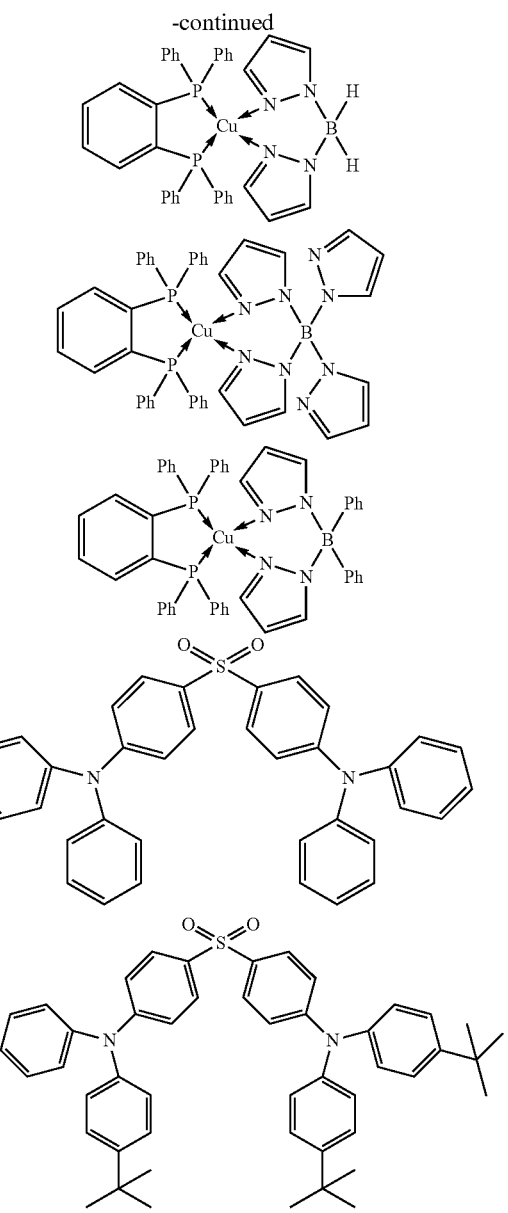

When the delayed fluorescent light-emitting material is used as a delayed fluorescent light-emitting dopant and the host material is contained, the content of the delayed fluorescent light-emitting dopant in the light-emitting layer desirably falls within the range of from 0.01 to 50 wt %, preferably from 0.1 to 20 wt %, more preferably from 0.01 to 10%.

The carborane compound represented by the general formula (1) can be used as the delayed fluorescent host material in the light-emitting layer. However, the delayed fluorescent host material may be selected from compounds other than the carborane. For example, the following compound can be used: a compound having a condensed aryl ring such as naphthalene, anthracene, phenanthrene, pyrene, chrysene, naphthacene, triphenylene, perylene, fluoranthene, fluorene, or indene, or a derivative thereof; an aromatic amine derivative such as N,N'-dinaphthyl-N,N'-diphenyl-4,4'-diphenyl-1,1'-diamine; a metal chelated oxinoid compound typified by tris(8-quinolinato)aluminum (III); a bisstyryl derivative such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative such as a polyphenylene vinylene derivative, a poly-p-phenylene derivative, a polyfluorene derivative, a polyvinyl carbazole derivative, a polythiophene derivative, or an arylsilane derivative. However, the delayed fluorescent host material is not particularly limited thereto. Further, a plurality of kinds of host materials may be used in combination.

When the light-emitting layer is a phosphorescent light-emitting layer, and the light-emitting layer contains a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold. Specific examples thereof include, but not limited to, the compounds disclosed in the following patent literatures.

For example, WO 2009/073245 A1, WO 2009/046266 A1, WO 2007/095118 A3, WO 2008/156879 A1, WO 2008/140657 A1, US 2008/261076 A1, JP 2008-542203 A, WO 2008/054584 A1, JP 2008-505925 A, JP 2007-522126 A, JP 2004-506305 A, JP 2006-513278 A, JP 2006-50596 A, WO 2006/046980 A1, WO 2005/113704 A3, US 2005/260449 A1, US 2005/2260448 A1, US 2005/214576 A1, WO 2005/076380 A3, US 2005/119485 A1, WO 2004/045001 A3, WO 2004/045000 A3, WO 2006/100888 A1, WO 2007/004380 A1, WO 2007/023659 A1, WO 2008/035664 A1, JP 2003-272861 A, JP 2004-111193 A, JP 2004-319438 A, JP 2007-2080 A, JP 2007-9009 A, JP 2007-227948 A, JP 2008-91906 A, JP 2008-311607 A, JP 2009-19121 A, JP 2009-46601 A, JP 2009-114369 A, JP 2003-253128 A, JP 2003-253129 A, JP 2003-253145 A, JP 2005-38847 A, JP 2005-82598 A, JP 2005-139185 A, JP 2005-187473 A, JP 2005-220136 A, JP 2006-63080 A, JP 2006-104201 A, JP 2006-111623 A, JP 2006-213720 A, JP 2006-290891 A, JP 2006-298899 A, JP 2006-298900 A, WO 2007/018067 A1, WO 2007/058080 A1, WO 2007/058104 A1, JP 2006-131561 A, JP 2008-239565 A, JP 2008-266163 A, JP 2009-57367 A, JP 2002-117978 A, JP 2003-123982 A, JP 2003-133074 A, JP 2006-93542 A, JP 2006-131524 A, JP 2006-261623 A, JP 2006-303383 A, JP 2006-303394 A, JP 2006-310479 A, JP 2007-88105 A, JP 2007-258550 A, JP 2007-324309 A, JP 2008-270737 A, JP 2009-96800 A, JP 2009-161524 A, WO 2008/050733 A1, JP 2003-73387 A, JP 2004-59433 A, JP 2004-155709 A, JP 2006-104132 A, JP 2008-37848 A, JP 2008-133212 A, JP 2009-57304 A, JP 2009-286716 A, JP 2010-83852 A, JP 2009-532546 A, JP 2009-536681 A, and JP 2009-542026 A.

Preferred examples of the phosphorescent light-emitting dopant include complexes such as Ir(ppy)$_3$, complexes such as Ir(bt)$_2$.acac$_3$, and complexes such as PtOEt$_3$, the complexes each having a noble metal element such as Ir as a central metal. Specific examples of those complexes are shown below, but the complexes are not limited to the compounds described below.

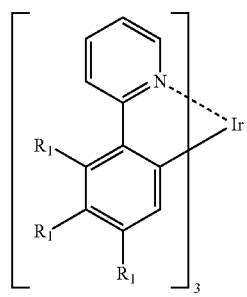

R$_1$: H, CH$_3$, CF$_3$, F

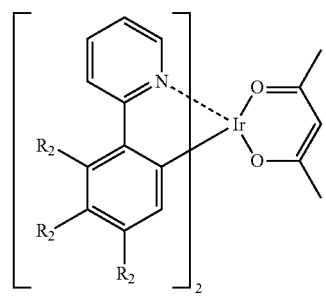

R$_2$: H, F

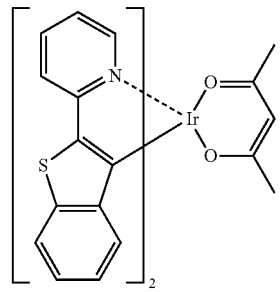

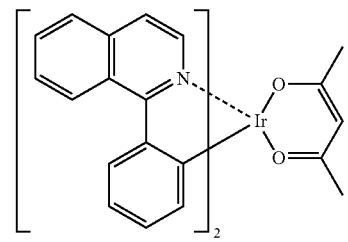

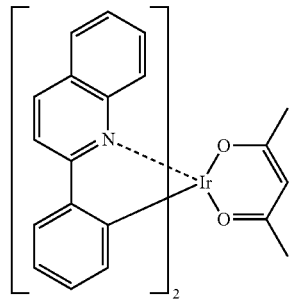

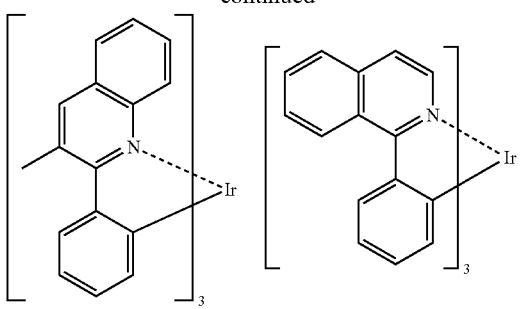
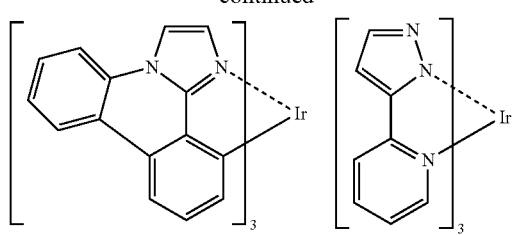
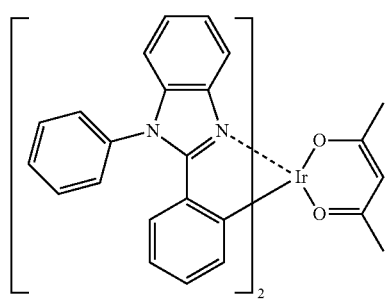
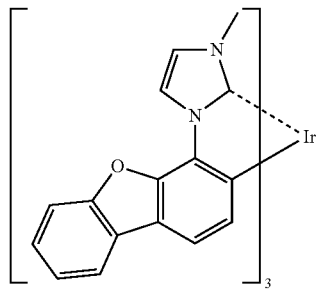
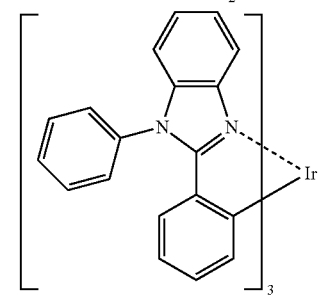
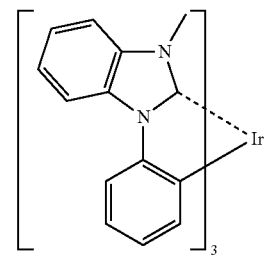
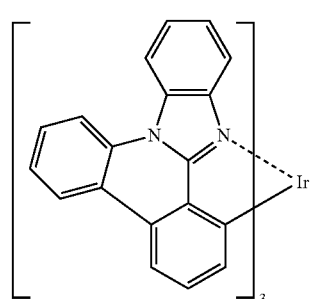
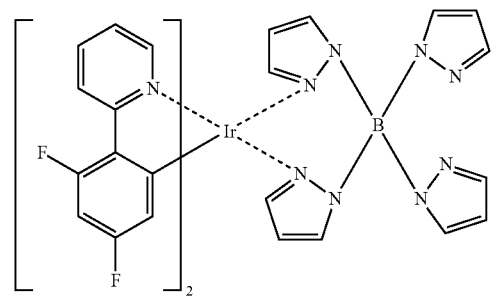
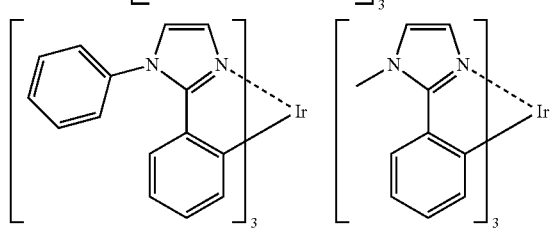
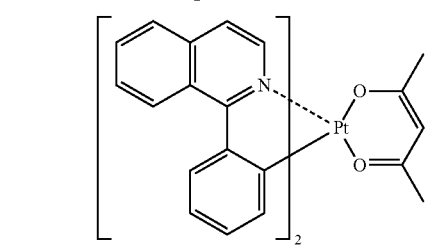
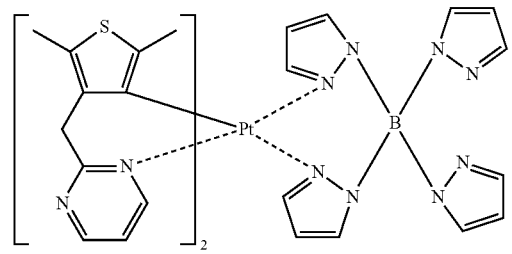

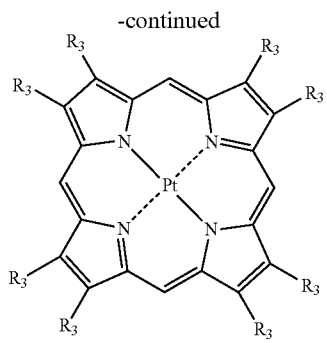

R₃: CH₃, CH₂CH₃

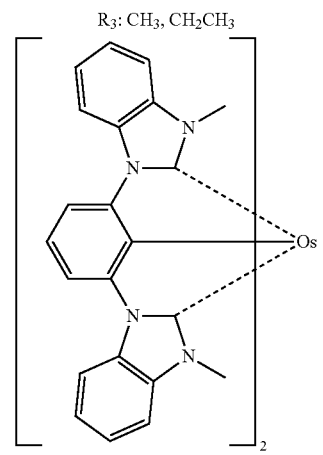

It is preferred that the content of the phosphorescent light-emitting dopant in the light-emitting layer fall within the range of from 0.1 to 50 wt %, more preferably from 1 to 30 wt %.

It is preferred to use, as the host material in the light-emitting layer, the carborane compound represented by any one of the general formulae (1) to (3). However, when the carborane compound is used in any of the organic layers other than the light-emitting layer, the material to be used in the light-emitting layer may be any other host material other than the carborane compound. Further, a plurality of kinds of known host materials may be used in combination.

Such other host materials are known because they are mentioned in many patent literatures and the like, and hence can be selected from those in the patent literatures and the like. Specific examples of the host material include, but not particularly limited to, an indole derivative, a carbazole derivative, an indolocarbazole derivative, a triazole derivative, an oxazole derivative, an oxadiazole derivative, an imidazole derivative, a polyarylalkane derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, a styrylamine derivative, an aromatic dimethylidene-based compound, a porphyrin-based compound, an anthraquinodimethane derivative, an anthrone derivative, a diphenylquinone derivative, a thiopyran dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly(N-vinylcarbazole) derivative, an aniline-based copolymer, a thiophene oligomer, a polythiophene derivative, a polyphenylene derivative, a polyphenylenevinylene derivative, and a polyfluorene derivative.

—Injecting Layer—

The injecting layer refers to a layer formed between an electrode and an organic layer for the purposes of lowering a driving voltage and improving light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

The carborane compound represented by any one of the general formulae (1) to (3) is preferably used in the hole-blocking layer. However, when the carborane compound is used in any other organic layer, a known hole-blocking material may be used. In addition, it is possible to use, as the hole-blocking material, any of materials for the electron-transporting layer to be described later as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

The carborane compound represented by any one of the general formulae (1) to (3) is preferably used in the electron-blocking layer. However, when the carborane compound is used in any other organic layer, a known electron-blocking material may be used. In addition, a material for the hole-transporting layer to be described later can be used as the electron-blocking material as required.

—Exciton-Blocking Layer—

The exciton-blocking layer refers to a layer used for blocking excitons produced by the recombination of a hole and an electron in the light-emitting layer from diffusing in charge-transporting layers. The insertion of this layer enables effective confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

As an exiton-blocking material, there are given, for example, 1,3-dicarbazolylbenzene (mCP) and bis(2-methyl-8-quinolinolato)-4-phenylphenolatoaluminum (III) (BAlq).

—Hole-Transporting Layer—

The hole-transporting layer is formed of a hole-transporting material having a function of transporting holes, and a single hole-transporting layer or a plurality of hole-transporting layers may be formed.

The hole-transporting material has any one of hole-injecting property, hole-transporting property, and electron-blocking property, and any of an organic compound and an inorganic compound may be used. It is preferred to use the carborane compound represented by any one of the general formulae (1) to (3) in the hole-transporting layer. However, any compound selected from conventionally known compounds may be used. Examples of the known hole-transporting material that may be used include a triazole derivative, an oxadiazole derivative, an imidazole derivative, a polyarylalkane derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a thiophene oligomer. However, a triazole derivative, an oxadiazole derivative, an imidazole derivative, or an arylamine derivative is preferably used, and an arylamine derivative is more preferably used.

—Electron-Transporting Layer—

The electron-transporting layer is formed of a material having a function of transporting electrons, and a single electron-transporting layer or a plurality of electron-transporting layers may be formed.

An electron-transporting material has a function of transferring electrons injected from the cathode into the light-emitting layer. Although the carborane compound represented by any one of the general formulae (1) to (3) is preferably used in the electron-transporting layer, any compound selected from conventionally known compounds may be used. Examples thereof include a nitro-substituted fluorene derivative, a diphenylquinone derivative, a carbodiimide derivative, a fluorenylidenemethane derivative, anthraquinodimethane and an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative that has a quinoxaline ring known as an electron withdrawing group. Further, it is also possible to use a polymer material in which any of those materials is introduced in a polymer chain or is used as a main chain.

EXAMPLES

Hereinafter, the present invention is described in more detail byway of Examples. It should be appreciated that the present invention is not limited to Examples below and may be carried out in various forms as long as the various forms do not deviate from the gist of the present invention.

The routes described below were used to synthesize a carborane compound to be used as an organic EL device material. It should be noted that the number of each compound corresponds to the number given to the chemical formula in the foregoing.

Example 1

Synthesis of Compound 30

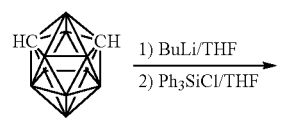

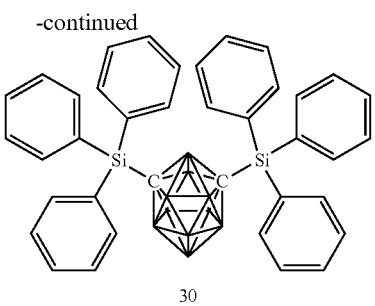

30

Under a nitrogen atmosphere, m-carborane (5.00 g, 0.0347 mol) and dry THF (50 ml) were loaded into a three-necked flask and cooled to 0° C. n-Butyllithium (51 ml, 0.0834 mol) was dropped to the mixture over 30 min. After the completion of the dropping, the mixture was stirred at 3° C. for 1 hr. A THF solution (250 ml) in which triphenylchlorosilane (28.66 g, 0.0972 mol) had been dissolved was dropped to the mixture over 20 min. After the completion of the dropping, the mixture was stirred at 26° C. for 4 hr. Water (50 ml) was added to the mixture and the whole was extracted with dichloromethane (50 ml×2). After that, an organic layer was dried with anhydrous magnesium sulfate and filtered, and then the filtrate was concentrated. The resultant residue was purified by silica gel column chromatography and recrystallization to provide the compound 30 (5.3 g, 23% yield) as a white solid.

Figure 2:
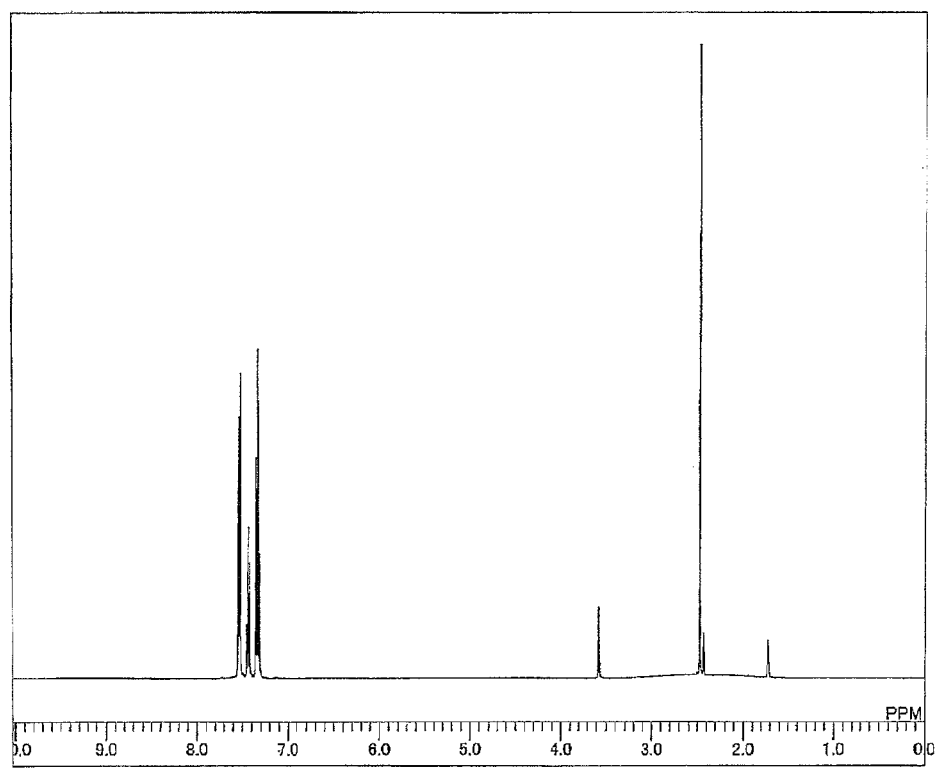
FIG. 2 shows a $^1$H-NMR chart of a carborane compound.

The FD-MS of the compound showed a peak at an m/z of 660. FIG. 2 shows the results of its 1H-NMR measurement (measurement solvent: THF-d8).

Example 2

Each thin film was laminated by a vacuum deposition method at a degree of vacuum of $4.0 \times 10^{-5}$ Pa on a glass substrate on which an anode formed of an ITO substrate having a thickness of 110 nm had been formed. First, CuPC was formed into a layer having a thickness of 20 nm on the ITO. Next, NPB was formed into a layer having a thickness of 20 nm to serve as a hole-transporting layer. Next, the compound 30 as a host material and Ir(ppy)$_3$ as a dopant were co-deposited from different deposition sources onto the hole-transporting layer to form a light-emitting layer having a thickness of 30 nm. At this time, the concentration of Ir(ppy)$_3$ was 10 wt %. Next, Alq3 was formed into a layer having a thickness of 40 nm to serve as an electron-transporting layer. Further, lithium fluoride (LiF) was formed into a layer having a thickness of 1 nm to serve as an electron-injecting layer on the electron-transporting layer. Finally, aluminum (Al) was formed into a layer having a thickness of 70 nm to serve as an electrode on the electron-injecting layer. Thus, an organic EL device was produced.

An external power source was connected to the resultant organic EL device to apply a DC voltage to the device. As a result, it was confirmed that the device had such light-emitting characteristics as shown in Table 1. A luminance, voltage, and luminous efficiency in Table 1 show values at the time of driving at 20 mA/cm$^2$. It was found that the local maximum wavelength of the emission spectrum of the device was 540 nm and hence light emission from Ir(ppy)$_3$ was obtained.

Examples 3 to 10

Organic EL devices were each produced in the same manner as in Example 2 except that compounds 1, 17, 18, 23, 48, 58, 59, and 102 were synthesized in the same manner as in Example 1 and the compound 1, 17, 18, 23, 48, 58, 59, or 102 was used instead of the compound 30 as the host material for the light-emitting layer in Example 2. It was found that the local maximum wavelength of the emission spectrum of each of the devices was 540 nm and hence light emission from Ir(ppy)$_3$ was obtained. Table 1 shows the respective characteristics.

Example 11 (Comparison)

An organic EL device was produced in the same manner as in Example 2 except that CBP was used as the host material for the light-emitting layer in Example 2. It was confirmed that the local maximum wavelength of the emission spectrum of the device was 535 nm and hence light emission from Ir(ppy)$_3$ was obtained. Table 1 shows its light-emitting characteristics.

Example 12 (Comparison)

An organic EL device was produced in the same manner as in Example 2 except that a compound H-1 was used as the host material for the light-emitting layer in Example. It was confirmed that the local maximum wavelength of the emission spectrum of the device was 540 nm and hence light emission from Ir(ppy)$_3$ was obtained. Table 1 shows its light-emitting characteristics.

H-1

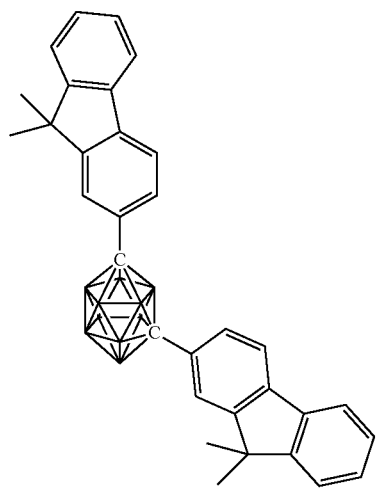

Example 2 is improved in initial characteristics as compared to Examples 11 and 12 as comparisons. The foregoing shows that the use of a compound having a silyl group on one carbon of a carborane in an organic EL device improves the characteristics of the organic EL device. The characteristics of the EL devices of Examples 3 to 10 are similarly good, which shows the superiority of the carborane compound represented by the general formula (1).

Example 13

Each thin film was laminated by a vacuum deposition method at a degree of vacuum of $4.0 \times 10^{-5}$ Pa on a glass substrate on which an anode formed of an ITO substrate having a thickness of 110 nm had been formed. First, CuPC was formed into a layer having a thickness of 20 nm on the ITO. Next, NPB was formed into a layer having a thickness of 20 nm to serve as a hole-transporting layer. Next, CBP as a host material and Ir(ppy)$_3$ as a dopant were co-deposited from different deposition sources onto the hole-transporting layer to form a light-emitting layer having a thickness of 30 nm. At this time, the concentration of Ir(ppy)$_3$ was 10 wt %. Then, the compound 58 was formed into a layer having a thickness of 10 nm to serve as a hole-blocking layer. Next, Alq3 was formed into a layer having a thickness of 30 nm to serve as an electron-transporting layer. Further, lithium fluoride (LiF) was formed into a layer having a thickness of 1 nm to serve as an electron-injecting layer on the electron-transporting layer. Finally, aluminum (Al) was formed into a layer having a thickness of 70 nm to serve as an electrode on the electron-injecting layer. Thus, an organic EL device was produced.

Examples 14 to 16

Organic EL devices were each produced in the same manner as in Example 13 except that the compound 27, 28, or 59 was used instead of the compound 58 as the hole-blocking layer of Example 13.

Example 17 (Comparison)

An organic EL device was produced in the same manner as in Example 13 except that bathocuproine (BCP) was used instead of the compound 58 as the hole-blocking layer of Example 13.

It was confirmed that the local maximum wavelength of the emission spectrum of each of the devices of Examples 14 to 17 was 540 nm and hence light emission from Ir(ppy)$_3$ was obtained. Table 2 shows their initial characteristics (at 20 mA/cm$^2$) as light-emitting characteristics.

TABLE 1

| Example | Host material compound | Luminance (cd/m$^2$) | Voltage (V) | Visual luminous efficiency (lm/W) |
| --- | --- | --- | --- | --- |
| 2 | 30 | 2630 | 9.0 | 4.6 |
| 3 | 1 | 1920 | 9.3 | 3.2 |
| 4 | 17 | 1880 | 9.2 | 3.2 |
| 5 | 18 | 2020 | 9.0 | 3.5 |
| 6 | 23 | 2400 | 8.9 | 4.2 |
| 7 | 48 | 2530 | 9.2 | 4.3 |
| 8 | 58 | 2660 | 8.8 | 4.7 |
| 9 | 59 | 2150 | 8.5 | 4.0 |
| 10 | 102 | 1960 | 8.6 | 3.6 |
| 11 | CBP | 1120 | 8.7 | 2.0 |
| 12 | H-1 | 1340 | 8.2 | 2.6 |

TABLE 2

| Example | Hole-blocking layer compound | Luminance (cd/m$^2$) | Voltage (V) | Visual luminous efficiency (lm/W) |
| --- | --- | --- | --- | --- |
| 13 | 58 | 3300 | 8.0 | 6.5 |
| 14 | 59 | 3100 | 8.3 | 5.9 |
| 15 | 27 | 2500 | 7.9 | 5.0 |
| 16 | 28 | 2550 | 8.0 | 5.0 |
| 17 | BCP | 2300 | 7.7 | 4.7 |

INDUSTRIAL APPLICABILITY

It is assumed that the carborane compound represented by the general formula (1) or (2) has a high triplet excitation energy (T1) because the compound has a silyl group on at least one carbon of a carborane, and the compound enables the fine adjustment of hole and electron mobilities, and the control of various energy values, i.e., an ionization potential (IP) and an electron affinity (EA) because the compound has specific substituents on the other carbon and on the silyl group. In addition, it may be possible to improve the stability of the carborane compound in each of active states, i.e., oxidation, reduction, and excitation, and at the same time, the compound has a good amorphous characteristic. As a result of the foregoing, the compound can realize an organic EL device having a long lifetime and high durability.

The organic EL device according to the present invention has light-emitting characteristics, driving lifetime, and durability at practically satisfactory levels. Thus, the organic EL device has a high technical value in applications to flat panel displays (display devices for portable phones, in-vehicle display devices, display devices for OA computers, televisions, and the like), light sources utilizing characteristics of planar light emitters (light sources in lighting equipment and copying machines and backlight sources in liquid crystal displays and instruments), sign boards, sign lamps, and the like.

The invention claimed is:

1. An organic electroluminescent device material, comprising a carborane compound represented by formula (1):

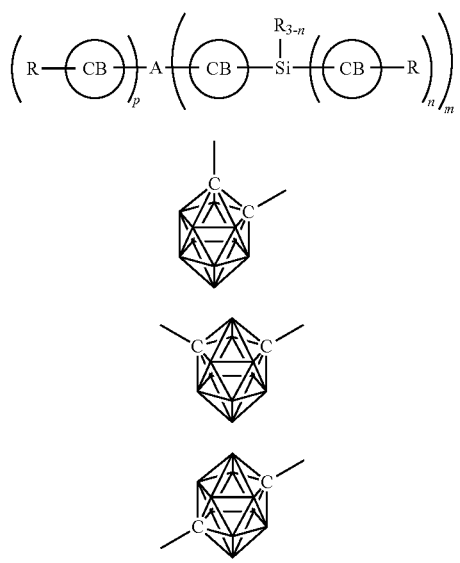

in formula (1):
a ring CB represents a divalent carborane group —$C_2B_{10}H_{10}$— represented by any one of the formula (a), the formula (b), and the formula (c), and when a plurality of rings CB are present in a molecule, the rings may be identical to or different from each other;
R represents a substituted or unsubstituted aliphatic hydrocarbon group having 1 to 12 carbon atoms, a substituted or unsubstituted aromatic hydrocarbon group having 6 to 50 carbon atoms, or a substituted or unsubstituted aromatic heterocyclic group having 3 to 50 carbon atoms, and a plurality of R's may be identical to or different from each other;
A represents a direct bond, an $Si(R)_d$ group, a substituted or unsubstituted aromatic hydrocarbon group having 6 to 50 carbon atoms, or a substituted or unsubstituted aromatic heterocyclic group having 3 to 50 carbon atoms, provided that A does not represent a direct bond except when p+m represents 2, and A represents a p+m-valent group when A represents a direct bond, R of the $Si(R)_d$ group has the same meaning as that of the R, and d represents an integer represented by 4−(p+m); and
p represents an integer of from 0 to 3, m represents an integer of from 1 to 4, n represents an integer of from 0 to 3, and p+m represents an integer of from 1 to 4.

2. An organic electroluminescent device material according to claim 1, wherein the organic electroluminescent device material comprises a carborane compound represented by formula (2):

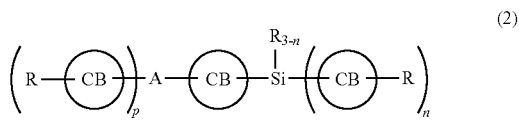

in formula (2), a ring CB, R, and A have the same meanings as those of the ring CB, R, and A of formula (1), p represents an integer of from 0 to 3, and n represents an integer of from 0 to 3.

3. An organic electroluminescent device material according to claim 1, wherein in formula (1), m represents 1 and the ring CB represents a divalent carborane group represented by the formula (b).

4. An organic electroluminescent device material according to claim 1, wherein in formula (1), p represents 0.

5. An organic electroluminescent device, comprising:
a substrate;
an anode;
an organic layer; and
a cathode,
the anode, the organic layer, and the cathode being laminated on the substrate,
wherein the organic layer comprises at least one layer selected from the group consisting of a light-emitting layer, a hole-transporting layer, an electron-transporting layer, an electron-blocking layer, and a hole-blocking layer, the at least one layer containing the organic electroluminescent device material according to claim 1.

6. An organic electroluminescent device according to claim 5, wherein the light-emitting layer contains the organic electroluminescent device material and a phosphorescent light-emitting dopant.

7. An organic electroluminescent device material according to claim 2, wherein p represents 1 or 2, and n represents 0 to 2.

8. An organic electroluminescent device material according to claim 2, wherein p represents 0, and n represents 0 to 2.

9. An organic electroluminescent device, comprising:
a substrate;
an anode;
an organic layer; and
a cathode,
the anode, the organic layer, and the cathode being laminated on the substrate,
wherein the organic layer comprises at least one layer selected from the group consisting of a light-emitting layer, a hole-transporting layer, an electron-transporting layer, an electron-blocking layer, and a hole-blocking layer, the at least one layer containing the organic electroluminescent device material according to claim 8.

* * * * *